(12) United States Patent
Bajic et al.

(10) Patent No.: US 11,733,247 B2
(45) Date of Patent: Aug. 22, 2023

(54) BREAKING OF DISULFIDE BONDS OF A NEBULIZED ANALYTE

(71) Applicant: Micromass UK Limited, Wilmslow (GB)

(72) Inventors: Stevan Bajic, Manchester (GB); Jeffery Mark Brown, Hyde (GB)

(73) Assignee: Micromass UK Limited, Wilmslow (GB)

( * ) Notice: Subject to any disclaimer, the term of this patent is extended or adjusted under 35 U.S.C. 154(b) by 793 days.

(21) Appl. No.: 16/604,933

(22) PCT Filed: Apr. 13, 2018

(86) PCT No.: PCT/GB2018/050991
§ 371 (c)(1),
(2) Date: Oct. 11, 2019

(87) PCT Pub. No.: WO2018/189558
PCT Pub. Date: Oct. 18, 2018

(65) Prior Publication Data
US 2021/0285956 A1    Sep. 16, 2021

(30) Foreign Application Priority Data
Apr. 13, 2017 (GB) .................. 1706002

(51) Int. Cl.
*H01J 49/10* (2006.01)
*G01N 33/68* (2006.01)
(Continued)

(52) U.S. Cl.
CPC ..... *G01N 33/6857* (2013.01); *G01N 30/7266* (2013.01); *G01N 33/6848* (2013.01);
(Continued)

(58) Field of Classification Search
CPC .......... G01N 30/7266; G01N 33/6848; G01N 33/6854; G01N 33/6857; H01J 49/0045;
(Continued)

(56) References Cited

U.S. PATENT DOCUMENTS 6,797,946 B2 * 9/2004 Apffel, Jr. ............. H01J 49/145
250/288
7,368,728 B2 5/2008 Simone et al.
(Continued)

FOREIGN PATENT DOCUMENTS

EP 0510510 A2 10/1992
EP 3249679 A1 11/2017
(Continued)

OTHER PUBLICATIONS

Li, Gongyu, et al. "Direct sequencing of a disulfide-linked peptide with electrospray ionization tandem mass spectrometry." Analyst 140.8 (2015): 2623-2627 (Year: 2015).*
(Continued)

*Primary Examiner* — Wyatt A Stoffa
(74) *Attorney, Agent, or Firm* — Goodwin Procter LLP

(57) ABSTRACT

A method of ionising a sample is disclosed comprising nebulising a sample which includes first biomolecules such as bovine insulin comprising one or more disulphide (S—S) bonds. A stream of droplet or charged droplets comprising one or more disulphide (S—S) bonds is directed so as to impact upon a target (106) or electrode so as to cause the breaking of a portion of the disulphide bonds. Alternatively, charged droplets may pass through an electric field region determined by an electrode (106) arranged downstream of a nebuliser or electrospray probe and an ion inlet (104) of a mass spectrometer so as to cause the breaking of a portion of the disulphide bonds.

19 Claims, 19 Drawing Sheets

(51) Int. Cl.
  *G01N 30/72* (2006.01)
  *H01J 49/00* (2006.01)
  *H01J 49/16* (2006.01)
  *H01J 49/06* (2006.01)
  *H01J 49/04* (2006.01)

(52) U.S. Cl.
  CPC ........ *H01J 49/0068* (2013.01); *H01J 49/045* (2013.01); *H01J 49/062* (2013.01); *H01J 49/165* (2013.01); *H01J 49/168* (2013.01)

(58) Field of Classification Search
  CPC .... H01J 49/0068; H01J 49/062; H01J 49/165; H01J 49/168; H01J 49/045
  See application file for complete search history.

(56) References Cited

U.S. PATENT DOCUMENTS

| | | | | |
|---|---|---|---|---|
| 8,921,777 | B2* | 12/2014 | Bajic | H01J 49/0445 250/288 |
| 9,305,761 | B2 | 4/2016 | Jarrell | |
| 10,546,740 | B2* | 1/2020 | Nishiguchi | G01N 27/623 |
| 11,239,066 | B2* | 2/2022 | Jones | A61B 18/1445 |
| 2006/0108539 | A1* | 5/2006 | Franzen | G01N 27/68 250/423 P |
| 2006/0145089 | A1* | 7/2006 | Cristoni | H01J 49/145 250/423 F |
| 2010/0012830 | A1* | 1/2010 | Cristoni | H01J 49/04 250/288 |
| 2010/0248388 | A1* | 9/2010 | Liu | H01J 49/0418 427/457 |
| 2011/0084203 | A1* | 4/2011 | Basile | H01J 49/142 530/344 |
| 2014/0339420 | A1* | 11/2014 | Bajic | H01J 49/24 250/288 |
| 2015/0048255 | A1* | 2/2015 | Jarrell | H01J 49/16 250/424 |
| 2015/0144780 | A1* | 5/2015 | Brown | H01J 49/0077 250/282 |
| 2016/0225601 | A1* | 8/2016 | Bajic | H01J 49/167 |
| 2016/0247668 | A1* | 8/2016 | Szalay | H01J 49/0454 |
| 2017/0084437 | A1 | 3/2017 | Glen et al. | |

FOREIGN PATENT DOCUMENTS

| | | |
|---|---|---|
| GB | 2349270 A | 10/2000 |
| GB | 2499681 A | 8/2013 |
| GB | 2507297 A | 4/2014 |
| JP | 2002190272 A | 7/2002 |
| JP | 2006329710 A | 12/2006 |
| WO | 2009003673 A2 | 1/2009 |
| WO | 2013005060 A2 | 1/2013 |
| WO | 2015128652 A1 | 9/2015 |
| WO | 2015128661 A1 | 9/2015 |

OTHER PUBLICATIONS

Combined Search and Examination Report under Section 17 for Application No. GB2003944.2 dated Mar. 31, 2020, 1 page.
Combined Search and Examination Report under Section 17 for Application No. GB2003945.9, dated Mar. 27, 2020, 1 page.
Combined Search and Examination Report for the United Kingdom Patent Application No. GB1806117.6, dated Dec. 24, 2018.
International Search Report and Written Opinion for International Application No. PCT/GB2018/050991, dated Jul. 12, 2018, 15 pages.
Eletskii, A. V., et al., "Dissociation of Molecules in Plasma and Gas: The Energy", Pure and Applied Chemistry, 57(9):1235-1244, Jan. 1, 1985.
Nicolardi, S., et al., "On-Line Electrochemical Reduction of Disulfide Bonds: Improved FTICR-CID and -ETD Coverage of Oxytocin and Hepcidin", J. Am. Soc. Mass Spectrom., 24:1980-1987 (2013).

* cited by examiner

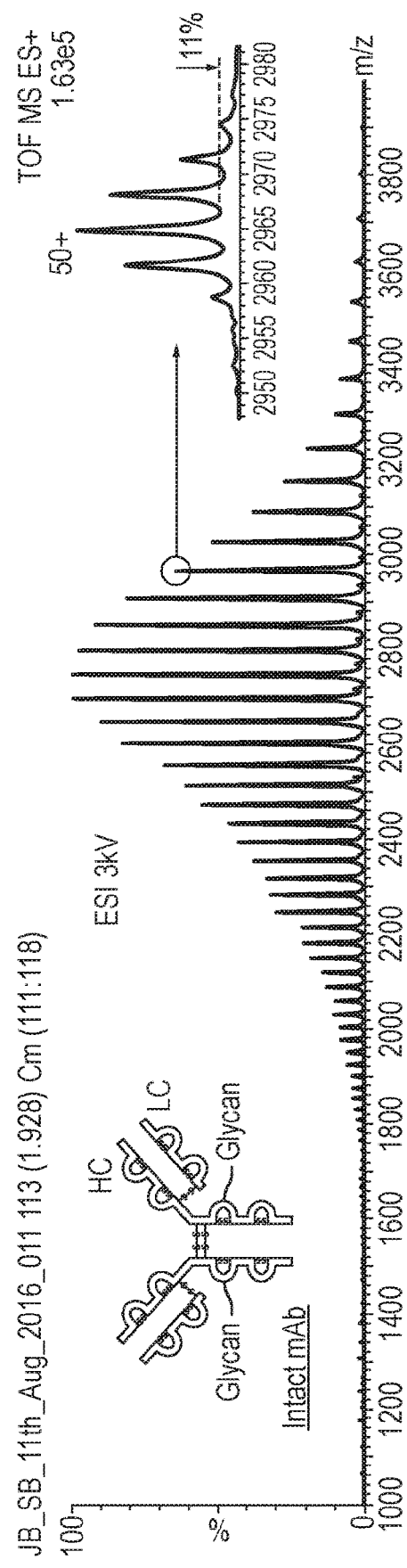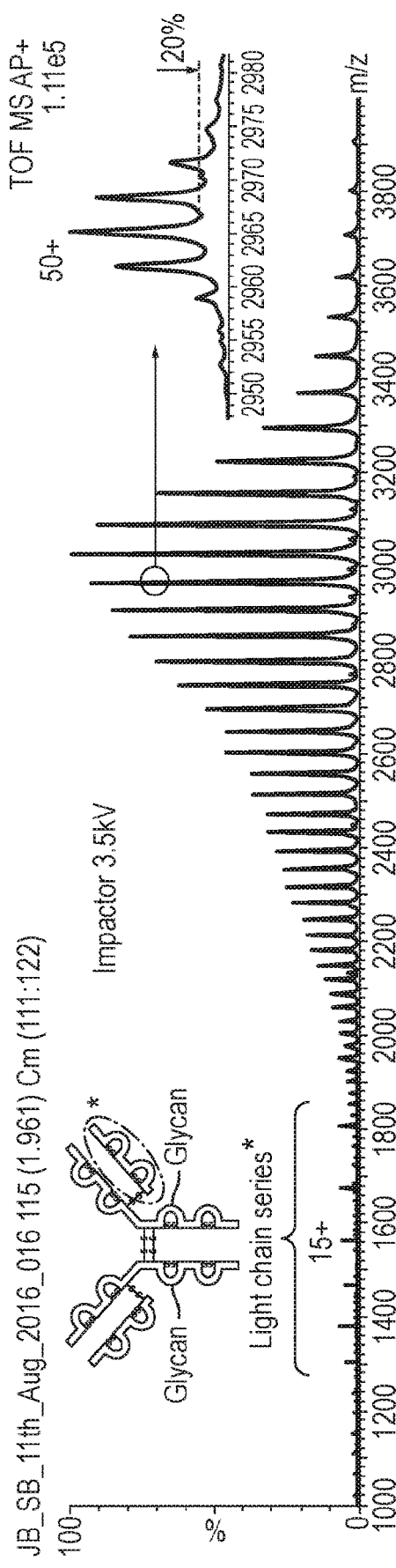

Primary structure of bovine insulin

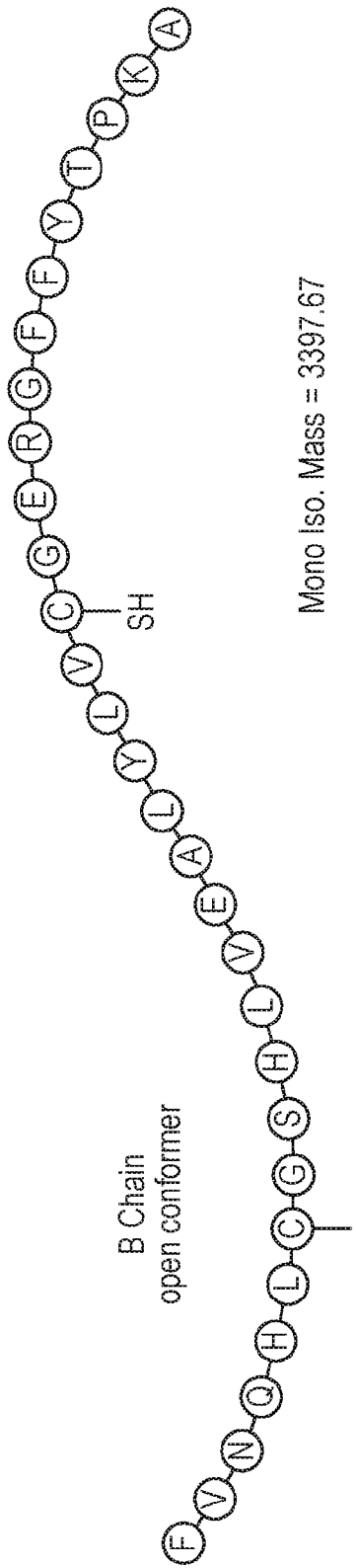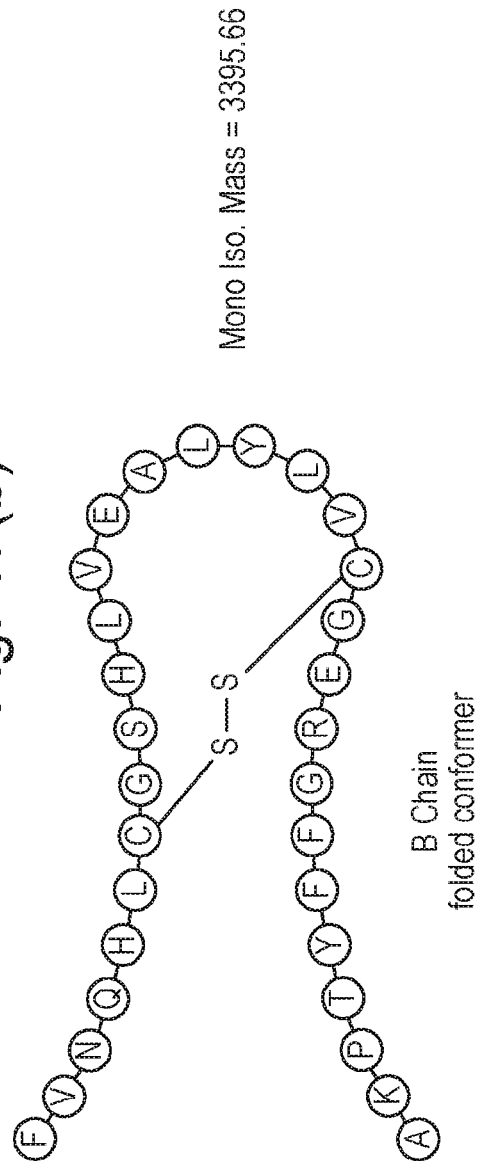
Fig. 17(a) B Chain open conformer Mono Iso. Mass = 3397.67
Fig. 17(b) B Chain folded conformer Mono Iso. Mass = 3395.66

Fig. 20(a)

N [F][V][N][Q][H][L][C][G][S][H][L][V][E][A][L][Y][L][V][C][G][E][R][G][F][F] 25
26[Y][T][P][K]A C
B Chain open conformer

Fig. 20(b)

```
            ┌────────S-S────────┐
N [F][V][N][Q][H][L][C]G S H L V E A L Y[L V [C][G][E][R]G F[F 25
26[Y][T][P][K A C
```
B Chain folded conformer

BREAKING OF DISULFIDE BONDS OF A NEBULIZED ANALYTE

CROSS-REFERENCE TO RELATED APPLICATION APPLICATIONS

This application is a national phase filing claiming the benefit of and priority to International Patent Application No. PCT/GB2018/050991, filed on Apr. 13, 2018, which claims priority from and the benefit of United Kingdom patent application No. 1706002.1 filed on Apr. 13, 2017. The contents of these applications are incorporated herein by reference.

FIELD OF THE INVENTION

The present invention relates generally to mass spectrometers and methods of mass spectrometry and in particular to methods of analysing biomolecules having disulphide bonds such as bovine insulin and monoclonal antibodies using mass spectrometry.

BACKGROUND

Monoclonal antibodies ("mAbs") are complex recombinant proteins that are increasingly used as therapeutics for many diseases. There are more than 30 products currently approved for marketing and hundreds of candidates are under clinical development in the pharmaceutical industry. Marketed therapeutic monoclonal antibodies predominantly comprise immunoglobulin G1 molecules ("IgG1"). Structurally, immunoglobulin molecules comprise two identical heavy chains ("HCs") and two identical light chains ("LCs"). Functionally, immunoglobulin consists of a crystallisable fragment ("Fc") and two identical antigen binding fragments ("Fabs") connected by a flexible hinge region. Each antigen binding fragment ("Fab") consists of one light chain ("LC") and the N-terminal half of one heavy chain ("Fd").

It is known to perform limited proteolysis of immunoglobulin molecules. The hinge region of immunoglobulin molecules is flexible and solvent-exposed allowing Fc, Fab and $F(ab')_2$ fragments to be generated by enzymatic cleavage under native conditions. Reduction of these large fragments results in three antibody domains each of ~25 kDa comprising light chain fragments ("LC"), monomeric crystallisable fragments ("Fc/2") and fragments comprising the N-terminal half of one heavy chain ("Fd"). These three fragments namely LC, Fc/2 and Fd may then be subjected to further analysis.

Monoclonal antibody products are extraordinarily heterogeneous and modifications in different domains of the antibody molecule can result in different biological consequences. Therefore, characterisation and routine monitoring of domain specific modifications is essential in order to ensure the quality of therapeutic antibody products.

It is known to use liquid chromatography coupled with mass spectrometry ("LC/MS") in combination with an Electrospray ionisation ("ESI") ion source in order to monitor the quality and safety of monoclonal antibodies during both the development and manufacturing cycles.

It is also known to use size exclusion chromatography/mass spectrometry ("SEC/MS") with aqueous mobile phases to analyse monoclonal antibodies in their native form. This technique produces simplified mass spectra that are significantly reduced in charge state and appear over a narrower mass to charge ratio range.

A recently discovered endopeptidase known as IdeS may be used to cleave heavy chains below the hinge region producing $F(ab')_2$ and Fc fragments. IdeS is a cysteine protease and an immunoglobulin-degrading enzyme of *Streptococcus pyogenes* which cleaves at the hinge region of all immunoglobulin subclasses. Following reduction of disulphide bonds, three antibody domains (LC, Fd and Fc/2) can be released for further characterisation. Accordingly, it is known to perform limited proteolysis of IgG molecules.

In addition to obtaining molecular weight information on the intact biomolecules, liquid chromatography mass spectrometry may be used in association with other processes such as Electron Transfer Dissociation ("ETD") and chemical reduction by diothioreitol ("DTT") in order to obtain structural information from monoclonal antibody fragments or fragment ions.

However, the conventional approach of obtaining additional structural information from monoclonal antibody fragments or fragment ions is relatively complex and/or time consuming.

Bovine insulin is a complex biomolecule that is commonly used as a substitute for human insulin in the treatment of diabetes. Differing from human insulin by three amino acid residues, bovine insulin produced for the treatment of diabetes is currently approved for market.

Structurally, bovine insulin is a two-chain polypeptide hormone comprising A and B chains connected via disulphide bonds and has a molecular weight of 5729.60 Da.

It is known to analyse large and complex biomolecules such as bovine insulin by collision-induced dissociation ("CID") and subsequent mass analysis.

However, the conventional approach of obtaining additional structural information from bovine insulin fragments or fragment ions is relatively complex.

It is therefore desired to provide an improved method of characterising and analysing large biomolecules having disulphide bonds such as bovine insulin and monoclonal antibodies.

SUMMARY

According to an aspect there is provided a method of ionising a sample comprising:

nebulising a sample which includes first biomolecules comprising one or more disulphide (S—S) bonds; and directing a stream of droplets or charged droplets having one or more disulphide (S—S) bonds so as either: (i) to impact upon a target or electrode so as to cause the breaking of a portion of the disulphide bonds; or (ii) to pass through an electric field region determined by an electrode arranged downstream of a nebuliser or electrospray probe and an ion inlet of a mass spectrometer so as to cause the breaking of a portion of the disulphide bonds.

The target or electrode may comprise aluminium.

The method may further comprise the step of introducing helium gas or a mixture including helium gas either: (i) into a nebuliser which is arranged to nebulise the sample; (ii) into the vicinity of the target or electrode; or (iii) into the electric field region.

The method may further comprise providing a target or electrode comprising one or more field enhancing features. The one or more field enhancing features may, for example, comprise one or more spikes, projections or sharp points.

The breaking of a portion of the disulphide bonds results in the fragmentation of a portion of the first biomolecules and/or conformational changes so as to form product or analyte ions. The product or analyte ions may comprise one or more of the following: (i) intact parent ions; (ii) A chain fragment ions; (iii) B chain fragment ions; (iv) modified parent ions; and (v) conformationally modified parent ions.

According to various embodiments the first biomolecules may comprise insulin molecules, bovine insulin molecules, human insulin molecules, equine insulin molecules, porcine insulin molecules, synthetic insulin molecules, monoclonal antibody molecules or Lysozyme. However, other embodiments are contemplated wherein other biomolecules having disulphide bonds may be analysed according to the various arrangements and methods disclosed herein.

The step of nebulising the sample may comprise either: (i) using an Electrospray impact ionisation ion source having a nebuliser or electrospray probe, wherein a first voltage is applied to the nebuliser or electrospray probe and a second lower, different or zero voltage is applied to the target or electrode; or (ii) using an impact ionisation ion source having a nebuliser, wherein a first or zero voltage is applied to the nebuliser and a second higher or different voltage is applied to the target or electrode.

The step of nebulising the sample may alternatively comprise using a Gap Electrospray ionisation ion source having a nebuliser or electrospray probe, wherein a first voltage is applied to the nebuliser or electrospray probe and a second lower, different or zero voltage is applied to the electrode.

The method may further comprise mass or mass to charge ratio selecting, filtering or otherwise preferentially selecting one or more (desired) species of product or analyte ions and optionally attenuating one or more other (undesired) species of product or analyte ions.

The step of mass or mass to charge ratio selecting, filtering or otherwise preferentially selecting one or more (desired) species of product or analyte ions may comprise using a quadrupole mass filter (or other form of mass or mass to charge ratio filter) to select product or analyte ions having a particular mass to charge ratio or range of mass to charge ratios.

The step of mass or mass to charge ratio selecting, filtering or otherwise preferentially selecting one or more (desired) species of product or analyte ions may comprise selecting, filtering or otherwise preferentially selecting either: (i) intact parent ions; and/or (ii) A chain fragment ions; and/or (iii) B chain fragment ions; and/or (iv) modified parent ions; and/or (v) conformationally modified parent ions. For example, according to an embodiment a mass filter may preferentially select B chain fragment ions whilst essentially attenuating intact parent ions and/or A chain fragment ions.

The method may further comprise temporally separating one or more (desired) species of product or analyte ions according to their ion mobility, differential ion mobility or collision cross section.

The method may further comprise colliding, fragmenting or reacting one or more species of product or analyte ions in one or more collision, fragmentation or reaction cells, wherein optionally the one or more collision, fragmentation or reaction cells are selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

According to another aspect there is provided a method of mass spectrometry comprising a method as claimed in any preceding claim.

According to another aspect there is provided an ion source comprising:
 a nebuliser or electrospray probe for nebulising a sample;
 an electrode arranged downstream of the nebuliser or electrospray probe; and
 an electric field region determined by the electrode and, in use, an ion inlet of a mass spectrometer, wherein in use a stream of charged droplets of first biomolecules comprising one or more disulphide (S—S) bonds is directed so as to pass through the electric field region without substantially impacting the electrode so as to form product or analyte ions.

The ion source may further comprise a device for introducing helium gas or a mixture including helium gas either: (i) into the nebuliser or electrospray probe; or (ii) into the electric field region.

According to another aspect there is provided a mass spectrometer comprising an ion source as described above, further comprising a mass or mass to charge ratio filter for selecting, filtering or otherwise preferentially selecting one or more species of product or analyte ions and optionally attenuating one or more other species of product or analyte ions. For example, the mass or mass to charge ratio filter may comprise a quadrupole mass filter. The quadrupole mass filter may comprise a quadrupole rod set mass filter or a segmented rod set mass filter. Other embodiments are contemplated wherein the mass filter may comprise a plurality of ring electrodes or other arrangements. For example, embodiments are contemplated wherein ions may pass through one or more apertures provided in the electrodes or the electrodes may be shaped such an ion guiding region is provided along the longitudinal length of the mass filter optionally in a direction parallel to an optic axis through the mass filter.

The mass spectrometer may further comprise a device for temporally separating one or more species of product or analyte ions according to their ion mobility, differential ion mobility or collision cross section. For example, the device may comprise an ion mobility spectrometer or separator ("IMS").

The mass spectrometer may further comprise one or more collision, fragmentation or reaction cells which are arranged to collide, fragment or react one or more species of product or analyte ions, wherein optionally the one or more collision, fragmentation or reaction cells are selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

According to another aspect there is provided an ion source comprising:

a nebuliser or electrospray probe for nebulising a sample;

a target or electrode arranged downstream of the nebuliser or electrospray probe;

wherein in use a stream of droplets emitted from the nebuliser or electrospray probe is directed to impact upon the target or electrode; and wherein the target or electrode further comprises one or more field enhancing features, optionally wherein the one or more field enhancing features comprise one or more spikes, projections or sharp points.

It should be understood that the provision of an ion mobility separator ("IMS") to separate analyte ions of interest in a temporal manner is desirable but not essential. Furthermore, although potentially a wide range of different collision, fragmentation or reaction cells may be utilised, according to various embodiments which are of particular interest a Collisional Induced Dissociation ("CID") or a Surface Induced Dissociation ("SID") fragmentation device or cell may be provided in order to fragment analyte ions of interest. The resulting fragment ions may then be mass analysed e.g. by an orthogonal acceleration Time of Flight mass analyser.

Accordingly, a number of embodiments are contemplated which are of particular interest and which comprise either CID/MS/MS analysis (i.e. selecting parent ions having a particular mass to charge ratio, subjecting the selected species of parent ions to CID (or SID or equivalent) fragmentation and then mass analysing the resultant fragment ions) or IMS-CID/MS/MS analysis (i.e. selecting parent ions having a particular mass to charge ratio, temporally separating the selected species of parent ions according to their ion mobility and then subjecting the parent ions which emerge from the ion mobility separator ("IMS") to CID (or SID or equivalent) fragmentation and then mass analysing the resultant fragment ions).

According to an aspect there is provided a method of ionising a sample comprising:

nebulising a sample which includes bovine insulin molecules; and directing a stream of bovine insulin droplets or charged droplets so as to impact upon a target or electrode so as to form product ions comprising one or more of the following: (i) intact parent bovine insulin ions; (ii) A chain fragment ions; and (iii) B chain fragment ions.

Therefore, according to various embodiments an Electrospray impact ionisation ion source may be used to produce parent and/or fragment ions of bovine insulin analytes. In particular, an Electrospray impact ionisation ion source may be utilised to produce both A chain fragment ions and B chain fragment ions by breaking the disulphide bridges of a bovine insulin molecule.

Using the known technique of Collision-induced dissociation ("CID"), the process of fragmenting ions which contain these disulphide bridges is comparatively much less effective.

As such, it is common for analysts to use alternative or complimentary techniques such as chemical reduction, electron capture dissociation ("ECD") or electrochemical cell technology. In the case of chemical reduction, the S—S bonds are cleaved in solution by adding a reducing agent such as dithiothreitol ("DTT") to the sample prior to CID/MS/MS analysis.

Advantageously, it has been demonstrated that according to various embodiments an Electrospray impact ionisation ion source may be used to produce certain types of bovine insulin parent and/or fragment ions which are not easily observable using a conventional Electrospray Ionisation ("ESI") ion source and according to a conventional method of analysis.

The various methods which are disclosed provide a novel and simple way of characterising biomolecules containing disulphide bridges, such as bovine insulin, without the need for additional sample preparation methods, charge reducing agents or complicated MS ion dissociation instrumentation (e.g. an Electron Transfer Dissociation fragmentation device).

The step of nebulising the sample may comprise using an Electrospray impact ionisation ion source having a nebuliser or electrospray probe, wherein a first voltage is applied to the nebuliser or electrospray probe and a second lower, different or zero voltage is applied to the target or electrode.

The first voltage may be in the range 3.0-6.0 kV and/or the second voltage may comprise 0 V or the target or electrode may be otherwise grounded. For example, according to an embodiment the first voltage may be in the range 3.0-3.1 kV, 3.1-3.2 kV, 3.2-3.3 kV, 3.3-3.4 kV, 3.4-3.5 kV, 3.5-3.6 kV, 3.6-3.7 kV, 3.7-3.8 kV, 3.8-3.9 kV, 3.9-4.0 kV, 4.0-4.1 kV, 4.1-4.2 kV, 4.2-4.3 kV, 4.3-4.4 kV, 4.4-4.5 kV, 4.5-4.6 kV, 4.6-4.7 kV, 4.7-4.8 kV, 4.8-4.9 kV, 4.9-5.0 kV, 5.0-5.1 kV, 5.1-5.2 kV, 5.2-5.3 kV, 5.3-5.4 kV, 5.4-5.5 kV, 5.5-5.6 kV, 5.6-5.7 kV, 5.7-5.8 kV, 5.8-5.9 kV or 5.9-6.0 kV.

Other embodiments are contemplated wherein the first voltage may be 6.0 kV.

According to another embodiment the step of nebulising the sample may comprise using an impact ionisation ion source having a nebuliser, wherein a first or zero voltage is applied to the nebuliser and a second higher or different voltage is applied to the target or electrode.

The first voltage may comprise 0 V or the target or electrode may otherwise be grounded and/or the second voltage may be in the range 3.0-6.0 kV. For example, according to an embodiment the second voltage may be in the range 3.0-3.1 kV, 3.1-3.2 kV, 3.2-3.3 kV, 3.3-3.4 kV, 3.4-3.5 kV, 3.5-3.6 kV, 3.6-3.7 kV, 3.7-3.8 kV, 3.8-3.9 kV, 3.9-4.0 kV, 4.0-4.1 kV, 4.1-4.2 kV, 4.2-4.3 kV, 4.3-4.4 kV, 4.4-4.5 kV, 4.5-4.6 kV, 4.6-4.7 kV, 4.7-4.8 kV, 4.8-4.9 kV, 4.9-5.0 kV, 5.0-5.1 kV, 5.1-5.2 kV, 5.2-5.3 kV, 5.3-5.4 kV, 5.4-5.5 kV, 5.5-5.6 kV, 5.6-5.7 kV, 5.7-5.8 kV, 5.8-5.9 kV or 5.9-6.0 kV.

Other embodiments are contemplated wherein the second voltage may be 6.0 kV.

According to another aspect there is provided a method of ionising a sample comprising:

nebulising a sample which includes bovine insulin molecules; and directing a stream of bovine insulin charged droplets so as to pass through an electric field region determined by an electrode arranged downstream of a nebuliser or electrospray probe and an ion inlet of a mass spectrometer so as to form product ions comprising one or more of the following: (i) intact parent bovine insulin ions; (ii) A chain fragment ions; and (iii) B chain fragment ions.

The step of nebulising the sample may comprise using a Gap Electrospray ionisation ion source having a nebuliser or electrospray probe, wherein a first voltage is applied to the nebuliser or electrospray probe and a second lower, different or zero voltage is applied to the electrode.

The first voltage may be in the range 4.0-6.0 kV and/or the second voltage may comprise 0 V or the electrode may otherwise be grounded. For example, according to an embodiment the first voltage may be in the range 4.0-4.1 kV, 4.1-4.2 kV, 4.2-4.3 kV, 4.3-4.4 kV, 4.4-4.5 kV, 4.5-4.6 kV, 4.6-4.7 kV, 4.7-4.8 kV, 4.8-4.9 kV, 4.9-5.0 kV, 5.0-5.1 kV, 5.1-5.2 kV, 5.2-5.3 kV, 5.3-5.4 kV, 5.4-5.5 kV, 5.5-5.6 kV, 5.6-5.7 kV, 5.7-5.8 kV, 5.8-5.9 kV or 5.9-6.0 kV.

Other embodiments are contemplated wherein the first voltage may be 6.0 kV.

The stream of bovine insulin charged droplets may according to various embodiments pass by the electrode without substantially impacting upon the electrode.

According to another embodiment of any of the above embodiments, the sample may be provided in the form of an eluent from a liquid chromatography separation device.

According to another aspect there is provided a method of mass spectrometry comprising a method as described above.

According to another aspect there is provided a method of critical quality attribute testing comprising:

nebulising a sample which includes bovine insulin molecules; and either: (i) directing a stream of bovine insulin droplets or charged droplets so as to impact upon a target or electrode; or (ii) directing a stream of bovine insulin charged droplets so as to pass through an electric field region determined by an electrode arranged downstream of a nebuliser or electrospray probe and an ion inlet of a mass spectrometer, so as to form product ions comprising one or more of the following: (i) intact parent bovine insulin ions; (ii) A chain fragment ions; and (iii) B chain fragment ions.

According to another aspect there is provided a method of critical quality attribute testing comprising:

ionising a sample which includes bovine insulin molecules; and identifying, recognising or detecting the presence of both: (i) intact parent bovine insulin ions; and (ii) A chain fragment ions; and/or (iii) B chain fragment ions.

According to an embodiment the B chain fragment ions may exist in at least two ion conformations comprising the following: (i) an open B chain ion conformation which does not include an S—S bond; and (ii) a folded B chain ion conformation which does include an S—S bond. According to an embodiment the method may comprise the further step of identifying, recognising or detecting the presence of (i) the open B chain ion conformation which does not include a S—S bond; and/or (ii) the folded B chain ion conformation which does include a S—S bond.

According to another embodiment the method may comprise the further step of analysing the product ions by ion mobility MS and/or MS/MS.

According to another aspect there is provided a method of ionising a sample comprising:

nebulising a sample which includes precursor molecules, wherein the precursor molecules include biomolecules comprising one or more disulphide (S—S) bonds; and directing a stream of precursor droplets or charged droplets so as to impact upon a target or electrode so as to cause the breaking of a portion of the S—S bonds, wherein the breaking of a portion of the S—S bonds results in the fragmentation of a portion of the precursor molecules to form product ions.

The portion may be between 0% and 100%.

The step of nebulising the sample may comprise using an Electrospray impact ionisation ion source having a nebuliser or electrospray probe, wherein a first voltage is applied to the nebuliser or electrospray probe and a second lower, different or zero voltage is applied to the target or electrode.

The first voltage may be in the range 3.0-6.0 kV and/or the second voltage may comprise 0 V or the target or electrode may be otherwise grounded. For example, according to an embodiment the first voltage may be in the range 3.0-3.1 kV, 3.1-3.2 kV, 3.2-3.3 kV, 3.3-3.4 kV, 3.4-3.5 kV, 3.5-3.6 kV, 3.6-3.7 kV, 3.7-3.8 kV, 3.8-3.9 kV, 3.9-4.0 kV, 4.0-4.1 kV, 4.1-4.2 kV, 4.2-4.3 kV, 4.3-4.4 kV, 4.4-4.5 kV, 4.5-4.6 kV, 4.6-4.7 kV, 4.7-4.8 kV, 4.8-4.9 kV, 4.9-5.0 kV, 5.0-5.1 kV, 5.1-5.2 kV, 5.2-5.3 kV, 5.3-5.4 kV, 5.4-5.5 kV, 5.5-5.6 kV, 5.6-5.7 kV, 5.7-5.8 kV, 5.8-5.9 kV or 5.9-6.0 kV.

Other embodiments are contemplated wherein the first voltage may be 6.0 kV.

According to another embodiment the step of nebulising the sample may comprise using an impact ionisation ion source having a nebuliser, wherein a first or zero voltage is applied to the nebuliser and a second higher or different voltage is applied to the target or electrode.

The first voltage may comprise 0 V or the target or electrode may otherwise be grounded and/or the second voltage may be in the range 3.0-6.0 kV. For example, according to an embodiment the second voltage may be in the range 3.0-3.1 kV, 3.1-3.2 kV, 3.2-3.3 kV, 3.3-3.4 kV, 3.4-3.5 kV, 3.5-3.6 kV, 3.6-3.7 kV, 3.7-3.8 kV, 3.8-3.9 kV, 3.9-4.0 kV, 4.0-4.1 kV, 4.1-4.2 kV, 4.2-4.3 kV, 4.3-4.4 kV, 4.4-4.5 kV, 4.5-4.6 kV, 4.6-4.7 kV, 4.7-4.8 kV, 4.8-4.9 kV, 4.9-5.0 kV, 5.0-5.1 kV, 5.1-5.2 kV, 5.2-5.3 kV, 5.3-5.4 kV, 5.4-5.5 kV, 5.5-5.6 kV, 5.6-5.7 kV, 5.7-5.8 kV, 5.8-5.9 kV or 5.9-6.0 kV.

Other embodiments are contemplated wherein the second voltage may be 6.0 kV.

According to another aspect there is provided a method of ionising a sample comprising:

nebulising a sample which includes precursor molecules, wherein the precursor molecules include biomolecules comprising one or more disulphide (S—S) bonds; and directing a stream of precursor charged droplets so as to pass through an electric field region determined by an electrode arranged downstream of a nebuliser or electrospray probe and an ion inlet of a mass spectrometer so as to cause the breaking of a portion of the S—S bonds wherein the breaking of a portion of the S—S bonds results in the fragmentation of a portion of the precursor molecules to form product ions.

The step of nebulising the sample may comprise using a Gap Electrospray ionisation ion source having a nebuliser or electrospray probe, wherein a first voltage is applied to the nebuliser or electrospray probe and a second lower, different or zero voltage is applied to the electrode.

The first voltage may be in the range 4.0-6.0 kV and/or the second voltage may comprise 0 V or the electrode may otherwise be grounded. For example, according to an embodiment the first voltage may be in the range 4.0-4.1 kV, 4.1-4.2 kV, 4.2-4.3 kV, 4.3-4.4 kV, 4.4-4.5 kV, 4.5-4.6 kV, 4.6-4.7 kV, 4.7-4.8 kV, 4.8-4.9 kV, 4.9-5.0 kV, 5.0-5.1 kV, 5.1-5.2 kV, 5.2-5.3 kV, 5.3-5.4 kV, 5.4-5.5 kV, 5.5-5.6 kV, 5.6-5.7 kV, 5.7-5.8 kV, 5.8-5.9 kV or 5.9-6.0 kV.

Other embodiments are contemplated wherein the first voltage may be 6.0 kV.

The stream of bovine insulin charged droplets may according to various embodiments pass by the electrode without substantially impacting upon the electrode.

The sample may be provided in the form of an eluent from a liquid chromatography separation device.

According to another aspect there is provided a method of mass spectrometry comprising a method as described above.

According to another embodiment there is provided a method as described above, wherein the precursor molecules comprise bovine insulin, and wherein the product ions comprise one or more of the following: (i) intact parent bovine insulin ions; (ii) A chain fragment ions; and (iii) B chain fragment ions.

The B chain fragment ions may exist in at least two ion conformations comprising the following: (i) an open B chain ion conformation which does not include a S—S bond; and (ii) a folded B chain ion conformation which does include a S—S bond.

The method may comprise the further step of identifying, recognising or detecting the presence of (i) the open B chain ion conformation which does not include a S—S bond; and/or (ii) the folded B chain ion conformation which does include a S—S bond.

According to another embodiment there is provided a method as described above, wherein the precursor molecules comprise monoclonal antibody molecules, and wherein the product ions comprise one or more of the following: (i) intact ("I") parent monoclonal antibody ions; (ii) intact minus light chain ("I-LC") parent monoclonal antibody ions; and (iii) light chain ("LC") fragment monoclonal antibody ions.

According to another embodiment there is provided a method as described above, comprising the further step of analysing the product ions by ion mobility MS and/or MS/MS.

In particular, it should be noted that the ability to straightforwardly and simply produce, recognise and analyse both parent intact bovine insulin ions and associated fragment bovine insulin ions represents a significant advance in the art, and further that the ability to straightforwardly and simply produce, recognise and analyse both parent intact biomolecule ions and associated fragment ions obtained by the breaking of S—S bonds represents a significant advance in the art.

Other embodiments are contemplated which comprise a method of critical quality attribute testing comprising:

nebulising a sample which includes bovine insulin molecules; and either: (i) directing a stream of bovine insulin droplets or charged droplets so as to impact upon a target or electrode; or (ii) directing a stream of bovine insulin charged droplets so as to pass through an electric field region determined by an electrode arranged downstream of a nebuliser or electrospray probe and an ion inlet of a mass spectrometer, so as to form product ions comprising one or more of the following: (i) intact parent bovine insulin ions; (ii) A chain fragment ions; and (iii) B chain fragment ions.

Other embodiments are contemplated which comprise a method of critical quality attribute testing comprising:

ionising a sample which includes bovine insulin molecules; and identifying, recognising or detecting the presence of both: (i) intact parent bovine insulin ions; and (ii) A chain fragment ions; and/or (iii) B chain fragment ions.

The spectrometer may comprise one or more continuous or pulsed ion sources.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise one or more collision, fragmentation or reaction cells for fragmenting analyte ions of interest selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The ion-molecule reaction device may be configured to perform ozonolysis for the location of olefinic (double) bonds in lipids.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (x) >about 10.0 MHz.

The spectrometer may comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a super-critical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

The electrodes may comprise electrodes which are formed on a printed circuit board, printed wiring board or an etched wiring board. For example, according to various embodiments the electrodes may comprise a plurality of traces applied or laminated onto a non-conductive substrate. The electrodes may be provided as a plurality of copper or metallic electrodes arranged on a substrate. The electrodes may be screen printed, photoengraved, etched or milled onto a printed circuit board or equivalent. According to an embodiment the electrodes may comprise electrodes arranged on a paper substrate impregnated with phenolic resin or a plurality of electrodes arranged on a fibreglass mat impregnated within an epoxy resin. More generally, the electrodes may comprise one or more electrodes arranged on a non-conducting substrate, an insulating substrate or a plastic substrate. According to embodiments the plurality of electrodes may be arranged on a substrate.

A plurality of insulator layers may be interspersed or interleaved between an array of electrodes. The plurality of electrodes may be arranged on or deposited on one or more insulator layers.

BRIEF DESCRIPTION OF THE DRAWINGS

Various embodiments together with other arrangements given for illustrative purposes only will now be described, by way of example only, and with reference to the accompanying drawings in which:

FIG. 5A shows a mass spectrum obtained in a conventional manner resulting from the summation of the mass spectra contained within the full width half maximum ("FWHM") of peak A as shown in FIG. 4 which was obtained using a conventional Electrospray ionisation ("ESI") ion source and FIG. 5B shows a corresponding mass spectrum which was obtained using an impact ionisation ion source for the same Trastuzumab sample and analytical method wherein the mass spectrum reveals the presence of light chain series ions in the mass range 1300-1900;

FIG. 17A shows a schematic of the structure of the "open" conformation of the bovine insulin B chain and FIG. 17B shows a schematic of the structure of the "closed" conformation of the bovine insulin B chain;

FIG. 20A shows a schematic of the cleaving structure of the open conformation of the bovine insulin B chain corresponding to the results of the MS/MS experiments of FIG. 18B and FIG. 20B shows a schematic of the cleaving structure of the folded confirmation of the bovine insulin B chain corresponding to the results of the MS/MS experiments of FIG. 18A;

DETAILED DESCRIPTION

Figure 1:
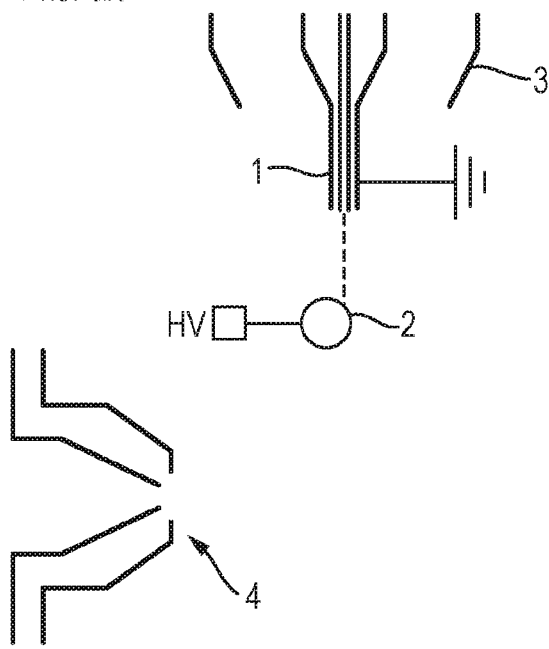
FIG. 1 shows a known impact ionisation spray source comprising a grounded nebuliser and a high voltage target.

Monoclonal antibodies ("mAbs") account for a significant proportion of the latest generation of therapeutic drugs that are based on large biomolecules. In contrast to small molecule drugs, monoclonal antibodies are derived from a fermentation process that leads to inherent heterogeneity which reinforces the need to characterise and monitor product quality during both the development and manufacturing cycles of monoclonal antibodies.

The combination of liquid chromatography and high resolution mass spectrometry ("LC/MS") may be employed as a monoclonal antibody analysis technique. In addition to obtaining molecular weight information concerning the intact biomolecules, LC/MS may be used in association with other processes, such as enzymatic IdeS (IdeS protease is an immunoglobulin-degrading enzyme from *Streptococcus pyogenes*), Electron Transfer Dissociation ("ETD") and chemical reduction by diothioreitol ("DTT") in order to obtain structural information from monoclonal antibody fragments and fragment ions.

Although the above known methods of obtaining structural information from monoclonal antibody fragments and fragment ions increase the ability to characterise monoclonal antibodies, such methods are problematic in that they are comparatively complex and increase the overall analysis time. Furthermore, in the case of, for example, Electron Transfer Dissociation such an approach requires the provision of a fragmentation cell.

In contrast to the known methods, methods according to various embodiments are disclosed below which are particularly advantageous in that they enable monoclonal antibody fragment ions to be readily produced via a simple and quick process which does not involve either a fragmentation cell (as is the case with Electron Transfer Dissociation ("ETD")), a chemical reduction method (such as using diothioreitol ("DTT")) or subjecting a sample of monoclonal antibody molecules to enzymatic cleavage prior to ionisation.

It will be understood, therefore, by those skilled in the art that the ability to quickly and simply produce, recognise and analyse both parent intact monoclonal antibody ions and associated fragment monoclonal antibody ions coupled with the ability to produce, recognise and analyse novel marker monoclonal antibody ions represents a significant advance in the art.

It is known to use Electrospray ionisation ("ESI") to ionise monoclonal antibody analytes. Electrospray ionisation results in the relatively gentle production of ions at atmospheric pressure and preserves the intact structure of biomolecules. Electrospray ionisation also produces multiply charged ions that allows large masses to be measured routinely on commercial mass spectrometers.

Impact ionisation ion sources are also known and involve generating a beam of droplets which are emitted from a pneumatic nebuliser. The beam of droplets are caused to impact upon a closely positioned target plate or cylindrical rod.

According to various embodiments which will be described in more detail below a conventional impact ionisation ion source, an Electrospray impact ionisation ion source and a Gap Electrospray ionisation ion source may be used to obtain mass spectral data directly from a sample of monoclonal antibodies. The monoclonal antibodies may be eluting from a liquid chromatography separation device. The mass spectral data which is obtainable according to various embodiments shows new additional structural information relating to monoclonal antibody analytes which is of particular interest and which is either not obtainable or which is at least not easily obtainable using conventional methods.

Impact Ionisation and Electrospray Impact Ionisation Ion Sources

FIG. 1 shows a conventional impact ionisation source which comprises a grounded pneumatic nebuliser 1 which is positioned in close proximity to a cylindrical high voltage target 2 such that the point of impact of a droplet beam emerging from the tip of the nebuliser 1 is asymmetric or off-axis with respect to the cylindrical axis. In one arrangement the distance between the tip of the nebuliser 1 and the surface of a 1.6 mm steel target 2 may be arranged to be 3 mm. The target 2 may be positioned 5 mm in front of and 7 mm above an inlet orifice 4 of a mass spectrometer as shown in FIG. 1.

It is also known to surround the nebuliser 1 with a heater 3 that delivers a flow of hot nitrogen gas to aid desolvation of the liquid droplets. Such an arrangement is also shown in FIG. 1.

Figure 2:
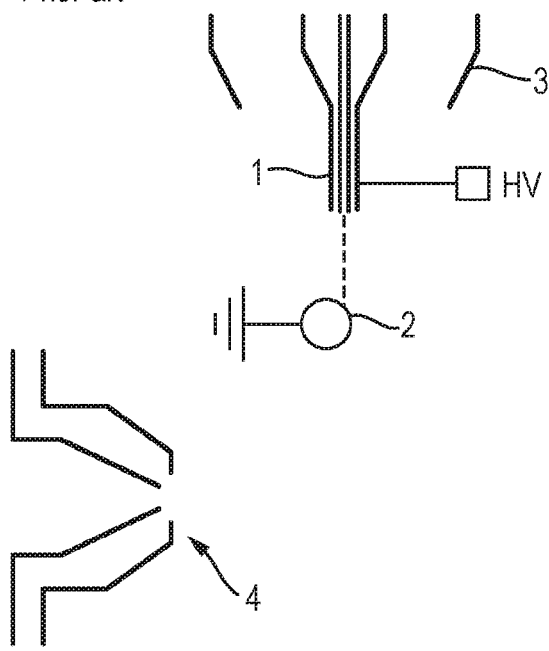
FIG. 2 shows a known Electrospray impact ionisation ion source comprising a high voltage nebuliser and a grounded target.

FIG. 2 shows a known Electrospray impact ionisation ion source which in terms of geometrical arrangement is similar to the impact ionisation ion source as shown in FIG. 1 except that the voltage supplies are reversed i.e. a high voltage is applied to the nebuliser 1 and the target 2 is grounded. The Electrospray impact ionisation arrangement as shown in FIG. 2 is known to be able significantly to reduce the charge state of multiply charged analytes. The degree of charge reduction is dependent upon the point of impact of charged droplets emerging from the nebuliser 1 on to the target 2.

Figure 3:
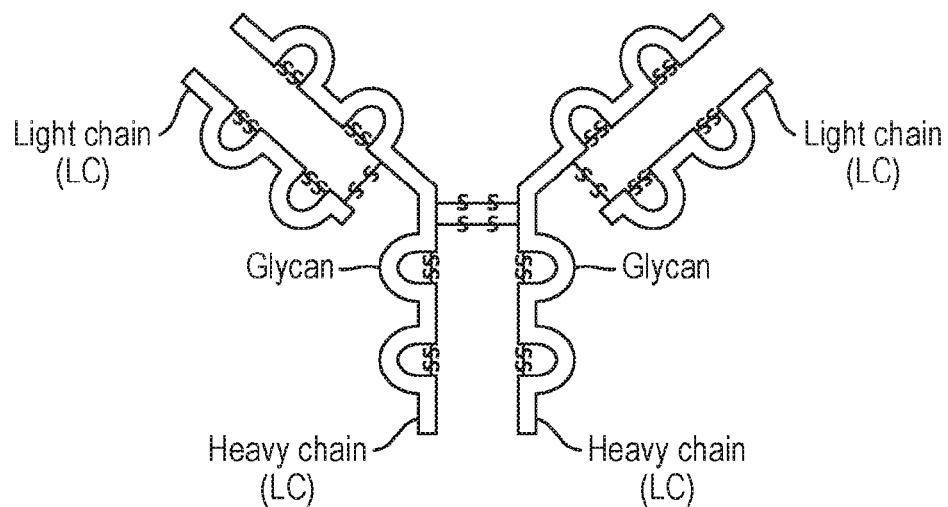
FIG. 3 shows a schematic of the structure of a monoclonal antibody molecule having a total molecular weight of ~150 kDa.

FIG. 3 shows a schematic of the structure of a monoclonal antibody molecule which has a molecular weight of ~150 kDa. The monoclonal antibody molecule comprises two identical heavy chains ("HCs") each having a molecular weight of ~50 kDa and two identical light chains ("LCs") each having a molecular weight of ~25 kDa. The main components are joined via disulphide bridges. The heavy chains are typically found to include N-linked biantennary glycans.

Analysis of Monoclonal Antibody Standards

A number of monoclonal antibody standards were analysed by a LC/MS method that utilised a ultra high pressure liquid chromatography ("UPLC") separation in combination with a quadrupole Time of Flight ("Q-TOF") mass spectrometer. Monoclonal antibody samples were prepared for analysis by diluting known monoclonal antibody standards in HPLC-grade water at a typical concentration of 1 mg/mL. However, it will also be understood that real biological matrices may similarly be tested and analysed according to various embodiments which are disclosed below. Real biological samples may optionally be subjected to additional sample clean-up techniques in order to reduce the level of background contamination ions in resulting mass spectra.

A 1 or 2 μL sample of different monoclonal antibody standards was injected onto a UPLC column (Waters Acquity®, 2.1 mm×50 mm, UPLC Protein BEH C4, 300, 1.7 μm) that was held at a temperature of 65° C. The sample was eluted using a time-varying flow rate and time-varying mobile phase composition (gradient elution), the details of which are shown below in Table 1.

TABLE 1

| Time (min) | Flow Rate (mL/min) | Mobile Phase % A | Mobile Phase % B |
|---|---|---|---|
| 0.00 | 0.5 | 95 | 5 |
| 0.50 | 0.5 | 95 | 5 |
| 0.51 | 0.2 | 95 | 5 |
| 2.00 | 0.2 | 5 | 95 |
| 2.50 | 0.5 | 5 | 95 |
| 2.60 | 0.5 | 95 | 5 |
| 3.00 | 0.5 | 5 | 95 |
| 3.10 | 0.5 | 95 | 5 |
| 3.60 | 0.5 | 5 | 95 |
| 3.70 | 0.5 | 95 | 5 |
| 4.50 | 0.5 | 95 | 5 |

Mobile phase A consisted of water with 0.1% formic acid and mobile phase B consisted of acetonitrile with 0.1% formic acid. Although the sample was injected at a 0.5 ml/min flow rate, sample elution into the ionisation source of the mass spectrometer occurred at a flow rate of 0.2 mL/min.

Figure 4:
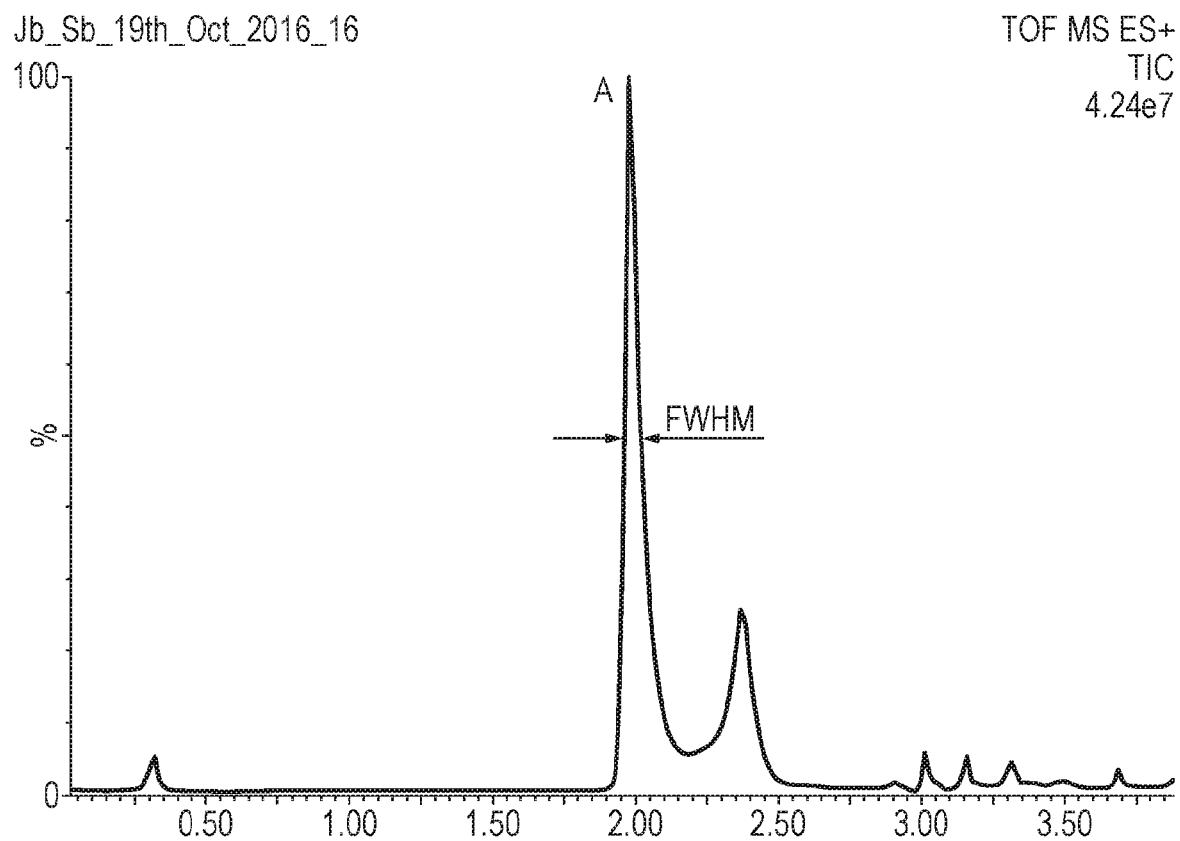
FIG. 4 shows an Electrospray ionisation mass spectrometry total ion chromatogram relating to the analysis of a 2 µL sample of the monoclonal antibody Trastuzumab.

FIG. 4 shows an Electrospray ionisation mass spectrometry total ion chromatogram for the analysis of a 2 μL sample of Trastuzumab monoclonal antibody according to the above method. Trastuzumab is a monoclonal antibody which is used in the treatment of breast cancer. A chromatographic peak was observed at a retention time of 1.95 min (peak A) as shown in FIG. 4 and corresponds to the main analyte ion signal from the Trastuzumab sample.

The various mass spectra contained within the full width half maximum ("FWHM") of peak A as shown in FIG. 4 were summed to produce an Electrospray ionisation mass spectrum as shown in FIG. 5A which corresponds to the intact ("I") parent monoclonal antibody ions.

The mass spectrum shown in FIG. 5A shows a multiply charged ion series that corresponds to intact ("I") parent monoclonal antibody ions. A zoomed region is shown in FIG. 5A and the zoomed spectrum for the 50+ charge states confirms that the monoclonal antibody is, in fact, composed of at least five main glycoforms that differ in nominal mass by 162 Da.

This type of UPLC-ESI-MS experiment and the corresponding mass spectrum shown in FIG. 5A may be considered essentially to be conventional for current monoclonal antibody analyses that are based on LC/MS.

Various embodiments will now be described with reference to FIG. 5B. According to various embodiments the Electrospray ionisation ion source which was used to obtain the conventional mass spectrum as shown in FIG. 5A was replaced with an impact ionisation ion source. The impact ionisation ion source was used to analyse the same Trastuzumab monoclonal antibody sample following the same analytical method as was used to obtain the mass spectral data shown in FIG. 5A. The impact ionisation ion source which was used was similar to the ion source as shown in FIG. 1.

As is apparent from FIG. 5B, the impact ionisation spray source produces the same multiply-charged intact ("I") parent monoclonal antibody ion series as is observed in FIG. 5A. Furthermore, the mass spectrum which is obtained has a comparable ion intensity (i.e. sensitivity) to that obtained using a conventional Electrospray ionisation ("ESI") source as shown in FIG. 5A.

However, in contrast to the mass spectrum shown in FIG. 5A, the mass spectrum shown in FIG. 5B which was obtained using an impact ionisation ion source according to various embodiments also shows both: (i) a small degree of charge reduction i.e. the mass spectrum is shifted to higher m/z relative to the mass spectrum shown in FIG. 5A; and (ii) importantly, in the mass to charge ratio range 1300-1900 a second multiply-charged ion series is observed.

The second multiply-charged ion series which is observed according to various embodiments is significant since the second observed ion series corresponds to an ionised light chain ("LC") component of Trastuzumab i.e. light chain fragment ions.

Reference is made back to FIG. 3 for further details of the light chain ("LC") component of monoclonal antibody molecules.

It will be apparent from comparing FIG. 5B with FIG. 5A that the second multiply-charged ion species which is observed in FIG. 5B across the mass range 1300-1900 (and which corresponds with the light chain ("LC") component of Trastuzumab monoclonal antibody) is not observed in the mass spectrum shown in FIG. 5A which was obtained in a conventional manner.

Accordingly, the method according to various embodiments enables a certain multiply-charged ion fragment species ("LC") of monoclonal antibodies to be easily and readily observed without requiring complex and time consuming sample preparation steps to be performed and/or without requiring a fragmentation device such as an Electron Transfer Dissociation ("ETD") fragmentation device to be provided. Furthermore, light chain fragment ions are readily observed without requiring a prior enzymatic cleavage step.

The various embodiments therefore are particularly advantageous in that the approach according to various embodiments enables the light chain ("LC") component of monoclonal antibody molecules to be readily observed by simply ionising the eluent from a liquid chromatography separation device without needing to subject the sample either to chemical reduction or enzymatic cleavage or requiring, for example, the provision of an Electron Transfer Dissociation ("ETD") fragmentation device and fragmenting parent monoclonal antibody ions within a vacuum chamber of a mass spectrometer.

A particular advantage of the various embodiments is that both conventional and new structural information relating to monoclonal antibody ions (or more generally relating to other types of biomolecules especially large biomolecules) can readily be obtained in a quick and simple manner.

The intensity of the light chain ("LC") series which is observed in FIG. 5B is typically found to increase as the target voltage or electrode voltage of the impact ionisation ion source is increased from 3 to 5 kV, wherein 5 kV is the maximum typical voltage applied to the target or electrode under standard operating conditions.

A particularly advantageous aspect of the various disclosed embodiments is, therefore, that by using an impact ionisation ion source it is possible to reveal additional structural information (e.g. observe light chain ("LC") ions) in a simple and quick process wherein such light chain ("LC") ions are not observed using a conventional Electrospray Ionisation ("ESI") source as is apparent from FIG. 5A (unless monoclonal antibody molecules are subjected to a prior enzymatic cleavage step which is a generally undesirable complication).

Example FDA Approved Therapeutic Monoclonal Antibodies

Table 2 below lists a number of FDA approved therapeutic monoclonal antibodies. It will be understood that currently there are hundreds of potential therapeutic monoclonal antibodies which are undergoing clinical trials prior to seeking FDA approval.

TABLE 2 abciximab
adalimumab
alemtuzumab
basiliximab
belimumab
bevacizumab
brentuximab vedotin
canakinumab
certolizumab pegol
cetuximab
daclizumab
daratumumab
denosumab
eculizumab
efalizumab
golimumab
ibritumomab tiuxetan
infliximab
ipilimumab (MDX-101)
muromonab-CD3
natalizumab
nivolumab
ofatumumab
omalizumab
palivizumab
panitumumab
Pembrolizumab
ranibizumab
rituximab
tocilizumab (or atlizumab)
tositumomab
trastuzumab
ustekinumab
vedolizumab The methods and apparatus which are disclosed in the present application are suitable for the enhanced detection and analysis of parent and fragment monoclonal antibody ions includes the above therapeutic monoclonal antibodies as well as other monoclonal antibodies, other biomolecules and other biotherapeutics.

Impact Ionisation and Electrospray Impact Ion Ionisation Ion Sources

U.S. Pat. No. 8,809,777 (Micromass), U.S. Pat. No. 8,921,777 (Micromass) and U.S. Pat. No. 9,082,603 (Micromass) disclose in more detail various aspects and details of impact ionisation ion sources and Electrospray impact ionisation ion sources which may be used according to various embodiments. The contents of these three patents are, therefore, incorporated herein by reference.

According to an embodiment an Electrospray impact ionisation ion source may be utilised wherein the ion source is electrically biased with a high voltage applied to the pneumatic sprayer and a grounded target similar to the Electrospray impact ionisation ion source as shown and described above with reference to FIG. 2. Such an Electrospray impact ionisation ion source can give rise to significantly higher charge reduction than is observed either with a standard impact ionisation ion source (as shown in FIG. 1) or a conventional Electrospray ionisation ("ESI") ion source.

An impact ionisation ion source and an Electrospray impact ionisation ion source as may be used according to various embodiments may comprise one or more nebulisers and one or more targets or electrodes. The one or more nebulisers may be arranged and adapted to emit, in use, a stream predominantly of droplets which are caused to impact upon the one or more targets or electrodes and to ionise the droplets so as to form a plurality of ions.

The droplets may comprise analyte droplets and the plurality of ions may comprise analyte ions. However, it is also contemplated that the droplets may comprise reagent droplets and the plurality of ions may comprise reagent ions. It is contemplated that any reagent ions which are created may react, interact with or transfer charge to neutral analyte molecules and cause the analyte molecules to become ionised. Reagent ions may also be used to enhance the formation of analyte ions.

Embodiments are contemplated wherein one or more tubes may be arranged and adapted to supply analyte(s) or other gases to a region adjacent the one or more targets or electrodes. Reagent ions may be arranged so as to ionise analyte gas so as to form a plurality of analyte ions.

An analyte liquid may be supplied to the one or more targets or electrodes and may be ionised to form a plurality of analyte ions and/or a reagent liquid may be supplied to the one or more targets or electrodes and may be ionised to form reagent ions which transfer charge to neutral analyte atoms or molecules to form analyte ions and/or which enhance the formation of analyte ions.

The one or more targets or electrodes may have one or more apertures and the analyte liquid and/or reagent liquid may be supplied directly to the one or more targets or electrodes. The liquid may be arranged so as to emerge from the one or more apertures. It is also contemplated that the one or more targets or electrodes may be coated with one or more liquid, solid or gelatinous analytes so that the one or more analytes are ionised so as to form a plurality of analyte ions. For example, it is contemplated that an monoclonal antibody sample may be coated on to a target plate or target cylinder and that the monoclonal antibody sample is that analysed by directing droplets from an impact ionisation ion source on to the target plate, target cylinder or electrode. It is also contemplated that the one or more targets or electrodes may be formed from one or more analytes and that the one or more analytes may be ionised to form a plurality of analyte ions.

The ion source which is used according to various embodiments may comprise an Atmospheric Pressure Ionisation ("API") ion source.

If an impact ionisation ion source is utilised then the one or more nebulisers may be arranged and adapted such that the majority of the mass or matter emitted by the one or more nebulisers is in the form of droplets not vapour. For example, at least 50%, 55%, 60%, 65%, 70%, 75%, 80%, 85%, 90% or 95% of the mass or matter emitted by the one or more nebulisers may be in the form of droplets. The one or more nebulisers may be arranged and adapted to emit a stream of droplets wherein the Sauter mean diameter ("SMD", d32) of the droplets is in a range: (i) <5 µm; (ii) 5-10 µm; (iii) 10-15 µm; (iv) 15-20 µm; (v) 20-25 µm; or (vi) >25 µm. The stream of droplets emitted from the one or more nebulisers may form a stream of secondary droplets after impacting the one or more targets or electrodes. The stream of droplets and/or the stream of secondary droplets may traverse a flow region with a Reynolds number (Re) in the range: (i) <2000; (ii) 2000-2500; (iii) 2500-3000; (iv) 3000-3500; (v) 3500-4000; or (vi) >4000. At the point of the droplets impacting the one or more targets or electrodes the droplets may have a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000. At the point of the droplets impacting the one or more targets or electrodes the droplets may have a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50. The mean axial impact velocity of the droplets upon the one or more targets or electrodes may be selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s. The one or more targets or electrodes may be arranged <20 mm, <19 mm, <18 mm, <17 mm, <16 mm, <15 mm, <14 mm, <13 mm, <12 mm, <11 mm, <10 mm, <9 mm, <8 mm, <7 mm, <6 mm, <5 mm, <4 mm, <3 mm or <2 mm from the exit of the one or more nebulisers.

The one or more nebulisers may be arranged and adapted to nebulise one or more eluents emitted by one or more devices over a period of time. The one or more devices may comprise one or more liquid chromatography separation devices. The one or more nebulisers may be arranged and adapted to nebulise one or more eluents, wherein the one or more eluents have a liquid flow rate selected from the group consisting of: (i) <1 (ii) 1-10 (iii) 10-50 µL/min; (iv) 50-100 µL/min; (v) 100-200 µL/min; (vi) 200-300 µL/min; (vii) 300-400 µL/min; (viii) 400-500 µL/min; (ix) 500-600 µL/min; (x) 600-700 µL/min; (xi) 700-800 µL/min; (xii) 800-900 µL/min; (xiii) 900-1000 µL/min; (xiv) 1000-1500 µL/min; (xv) 1500-2000 µL/min; (xvi) 2000-2500 µL/min; and (xvii) >2500 µL/min. The one or more nebulisers may according to other embodiments comprise one or more rotating disc nebulisers.

The one or more nebulisers may comprise a first capillary tube having an exit which emits, in use, the stream of droplets. The first capillary tube may maintained, in use, at a potential: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV.

The first capillary tube may be maintained, in use, at a potential of: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV; relative to the potential of an enclosure surrounding the ion source and/or an ion inlet device which leads to a first vacuum stage of a mass spectrometer and/or the one or more targets.

According to an embodiment a wire may be located within the volume enclosed by the first capillary tube wherein the wire is arranged and adapted to focus the stream of droplets. The first capillary tube may be surrounded by a second capillary tube which is arranged and adapted to provide a stream of gas to the exit of the first capillary tube. Alternatively, the second capillary tube may be arranged and adapted to provide a cross flow stream of gas to the exit of the first capillary tube. The second capillary tube may surround the first capillary tube and/or may be either concentric or non-concentric with the first capillary tube. The ends of the first and second capillary tubes may be either: (i) flush or parallel with each other; or (ii) protruded, recessed or non-parallel relative to each other.

The exit of the first capillary tube may have a diameter D and the spray of droplets may be arranged to impact on an impact zone of the one or more targets or electrodes. The impact zone may have a maximum dimension of x and wherein the ratio x/D is in the range <2, 2-5, 5-10, 10-15, 15-20, 20-25, 25-30, 30-35, 35-40 or >40. The impact zone may have an area selected from the group consisting of: (i) <0.01 mm$^2$; (ii) 0.01-0.10 mm$^2$; (iii) 0.10-0.20 mm$^2$; (iv) 0.20-0.30 mm$^2$; (v) 0.30-0.40 mm$^2$; (vi) 0.40-0.50 mm$^2$; (vii) 0.50-0.60 mm$^2$; (viii) 0.60-0.70 mm$^2$; (ix) 0.70-0.80 mm$^2$; (x) 0.80-0.90 mm$^2$; (xi) 0.90-1.00 mm$^2$; (xii) 1.00-1.10 mm$^2$; (xiii) 1.10-1.20 mm$^2$; (xiv) 1.20-1.30 mm$^2$; (xv) 1.30-1.40 mm$^2$; (xvi) 1.40-1.50 mm$^2$; (xvii) 1.50-1.60 mm$^2$; (xviii) 1.60-1.70 mm$^2$; (xix) 1.70-1.80 mm$^2$; (xx) 1.80-1.90 mm$^2$; (xxi) 1.90-2.00 mm$^2$; (xxii) 2.00-2.10 mm$^2$; (xxiii) 2.10-2.20 mm$^2$; (xxiv) 2.20-2.30 mm$^2$; (xxv) 2.30-2.40 mm$^2$; (xxvi) 2.40-2.50 mm$^2$; (xxvii) 2.50-2.60 mm$^2$; (xxviii) 2.60-2.70 mm$^2$; (xxix) 2.70-2.80 mm$^2$; (xxx) 2.80-2.90 mm$^2$; (xxxi) 2.90-3.00 mm$^2$; (xxxii) 3.00-3.10 mm$^2$; (xxxiii) 3.10-3.20 mm$^2$; (xxxiv) 3.20-3.30 mm$^2$; (xxxv) 3.30-3.40 mm$^2$; (xxxvi) 3.40-3.50 mm$^2$; (xxxvii) 3.50-3.60 mm$^2$; (xxxviii) 3.60-3.70 mm$^2$; (xxxix) 3.70-3.80 mm$^2$; (xl) 3.80-3.90 mm$^2$; and (xli) 3.90-4.00 mm$^2$.

The ion source may further comprise one or more heaters which are arranged and adapted to supply one or more heated streams of gas to the exit of the one or more nebulisers. The one or more heaters may surround the first capillary tube and may be arranged and adapted to supply a heated stream of gas to the exit of the first capillary tube. The one or more heaters may comprise one or more infra-red heaters or one or more combustion heaters. The ion source may further comprise one or more heating devices arranged and adapted to directly and/or indirectly heat the one or more targets or electrodes. The one or more heating devices may comprise one or more lasers arranged and adapted to emit one or more laser beams which impinge upon the one or more targets or electrodes in order to heat the one or more targets or electrodes.

The one or more targets or electrodes may be maintained, in use, at a potential: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV. The one or more targets or electrodes may be maintained, in use, at the above potentials relative to the potential of an enclosure surrounding the ion source and/or an ion inlet device which leads to a first vacuum stage of a mass spectrometer and/or the one or more nebulisers.

The one or more targets or electrodes may be maintained at a positive potential and the droplets impacting upon the one or more targets or electrodes may form a plurality of positively charged ions. Alternatively, according to another mode of operation the one or more targets or electrodes may be maintained at a negative potential and the droplets impacting upon the one or more targets or electrodes form a plurality of negatively charged ions. The ion source may further comprise a device arranged and adapted to apply a sinusoidal or non-sinusoidal AC or RF voltage to the one or more targets or electrodes.

The one or more targets or electrodes may be arranged or otherwise positioned so as to deflect the stream of droplets and/or the plurality of ions towards an ion inlet device of a mass spectrometer. The one or more targets or electrodes may be positioned upstream of an ion inlet device of a mass spectrometer so that ions are deflected towards the direction of the ion inlet device. The one or more targets or electrodes may comprise a stainless steel target, a metal, gold, a non-metallic substance, a semiconductor, a metal or other substance with a carbide coating, an insulator or a ceramic. The one or more targets or electrodes may comprise a plurality of target elements or electrodes so that droplets from the one or more nebulisers cascade upon a plurality of target elements or electrodes and/or wherein the target or electrodes is arranged to have multiple impact points so that droplets are ionised by multiple glancing deflections.

The one or more targets or electrodes may be shaped or have an aerodynamic profile so that gas flowing past the one or more targets or electrodes is directed or deflected towards, parallel to, orthogonal to or away from an ion inlet device of a mass spectrometer. At least some or a majority of the plurality of ions may be arranged so as to become entrained, in use, in the gas flowing past the one or more targets or electrodes. According to an embodiment in a mode of operation droplets from one or more reference or calibrant nebulisers may be directed onto the one or more targets or electrodes. In a mode of operation droplets from one or more analyte nebulisers may be directed onto the one or more targets or electrodes.

A mass spectrometer may be arranged downstream of the impact ionisation source, Electrospray impact ionisation ion source or Gap Electrospray ionisation ion source. The mass spectrometer may comprise an ion inlet device which leads to a first vacuum stage of the mass spectrometer. The ion inlet device may comprises an ion orifice, an ion inlet cone, an ion inlet capillary, an ion inlet heated capillary, an ion tunnel, an ion mobility spectrometer or separator, a differential ion mobility spectrometer, a Field Asymmetric Ion Mobility Spectrometer ("FAIMS") device or other ion inlet.

The one or more targets or electrodes may be located at a first distance $X_1$ in a first direction from the ion inlet device and at a second distance $Z_1$ in a second direction from the ion inlet device, wherein the second direction is orthogonal to the first direction and wherein: (i) $X_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm; and/or (ii) $Z_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm.

The one or more targets or electrodes may be positioned so as to deflect the stream of droplets and/or the plurality of ions towards the ion inlet device. The one or more targets or electrodes may be positioned upstream of the ion inlet device. The one or more targets or electrodes may comprise either: (i) one or more rods; or (ii) one or more pins having a taper cone. The stream of droplets may arranged to impact the one or more rods or the taper cone of the one or more pins either: (i) directly on the centreline of the one or more rods or pins; or (ii) on the side of the one or more rods or the taper cone of the one or more pins which faces towards or away from the ion inlet orifice.

The mass spectrometer may further comprise an enclosure enclosing the one or more nebulisers, the one or more targets or electrodes and the ion inlet device. The mass spectrometer may further comprise one or more deflection or pusher electrodes, wherein in use one or more DC voltages or DC voltage pulses are applied to the one or more deflection or pusher electrodes in order to deflect or urge ions towards an ion inlet device of the mass spectrometer.

It is also contemplated that the above ion sources may be used to at least partially desolvate or further desolvate a stream of droplets. The resulting gas phase molecules and/or secondary droplets may be subsequently ionised by a separate ion source.

For completeness, it will be understood by those skilled in the art that a conventional ion source known as a SACI ion source emits a vapour stream and that the impact velocity of the vapour emitted from a SACI ion source upon a target is relatively low and is approximately 4 m/s. By way of contrast, an impact ionisation ion source according to various embodiments does not emit a vapour stream but instead emits a high density droplet stream. Furthermore, the impact velocity of the droplet stream upon a target or electrode is relatively high and may be approximately 100 m/s. It will be apparent, therefore, that an impact ionisation source according to various embodiments is quite distinct from other types of known ion sources such as SACI ion sources.

According to various embodiments an impact ionisation ion source may be used which converts a liquid stream into a nebulised spray via a concentric flow of high velocity gas without the aid of a high potential difference at the sprayer or nebuliser tip. A micro target or electrode with comparable dimensions or impact zone to the droplet stream may positioned in close proximity (e.g. <5 mm) to the sprayer tip to define an impact zone and to partially deflect the spray towards the ion inlet orifice of a mass spectrometer. The resulting ions and charged droplets may be sampled by the first vacuum stage of the mass spectrometer.

The target or electrode may comprise a stainless steel target or electrode. However, other embodiments are contemplated wherein the target or electrode may comprise other metallic substances (e.g. gold) and non-metallic substances. Embodiments are contemplated, for example, wherein the target or electrode comprises a semiconductor, a metal or other substance with a carbide coating, an insulator or a ceramic.

According to another embodiment the target or electrode may comprise a plurality of plates, target elements or electrodes so that droplets from the nebuliser cascade upon a plurality of target plate, target elements or electrodes. According to this embodiment there may be multiple impact points and droplets may be ionised by multiple glancing deflections.

From an API source perspective, the combination of a close-coupled impact ionisation ion source which also serves as a charged ionization surface provides the basis of a sensitive multimode ionization source. The spray tip and micro target or electrode may be configured in close proximity with a glancing impact geometry which results in increased spray flux at the target or electrode and significantly less beam divergence or reflected dispersion.

The ion sources which may be used according to various embodiments may comprise a multimode ion source which advantageously can ionise high and low polarity analytes at high efficiency without the need to switch hardware or tuning parameters. The droplets which impact the one or more targets or electrodes may be uncharged.

Charge Reduction Utilising an Electrospray Impact Ionisation Ion Source

According to various embodiments an Electrospray impact ionisation ion source may be utilised to ionise a monoclonal antibody sample and generate intact ("I") parent monoclonal antibody ions, intact minus light chain ("I-LC") parent monoclonal antibody ions and light chain ("LC") fragment monoclonal antibody ions. In particular, according to various embodiments an Electrospray impact ionisation ion source may be utilised in order to reduce the charge state of the parent and/or fragment ions which makes the ions easier to mass analyse.

The beneficial effects of charge reduction which may be obtained or observed using an Electrospray impact ionisation ion source according to various embodiments will now be illustrated in more detail with reference to FIGS. 6A and 6B.

Figure 6A:
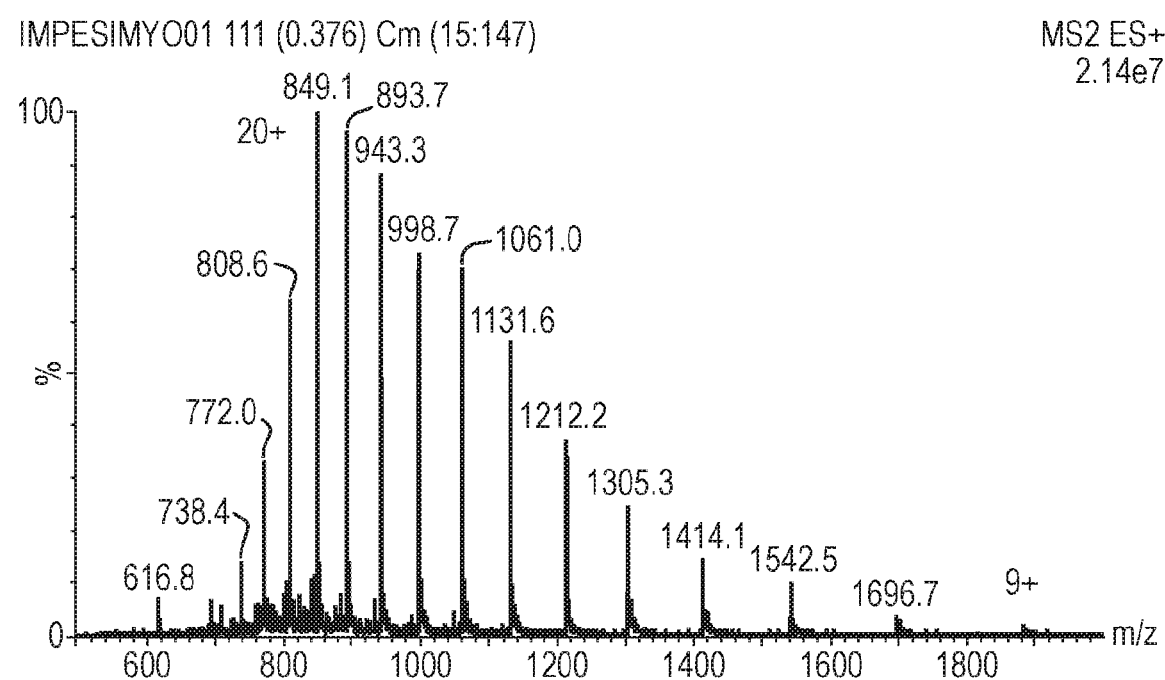
FIG. 6A shows a mass spectrum for the non-antibody protein sample Horse Heart Myoglobin ("HHM") which was obtained by tuning an Electrospray impact ionisation ion source for maximum ion intensity.
Figure 6B:
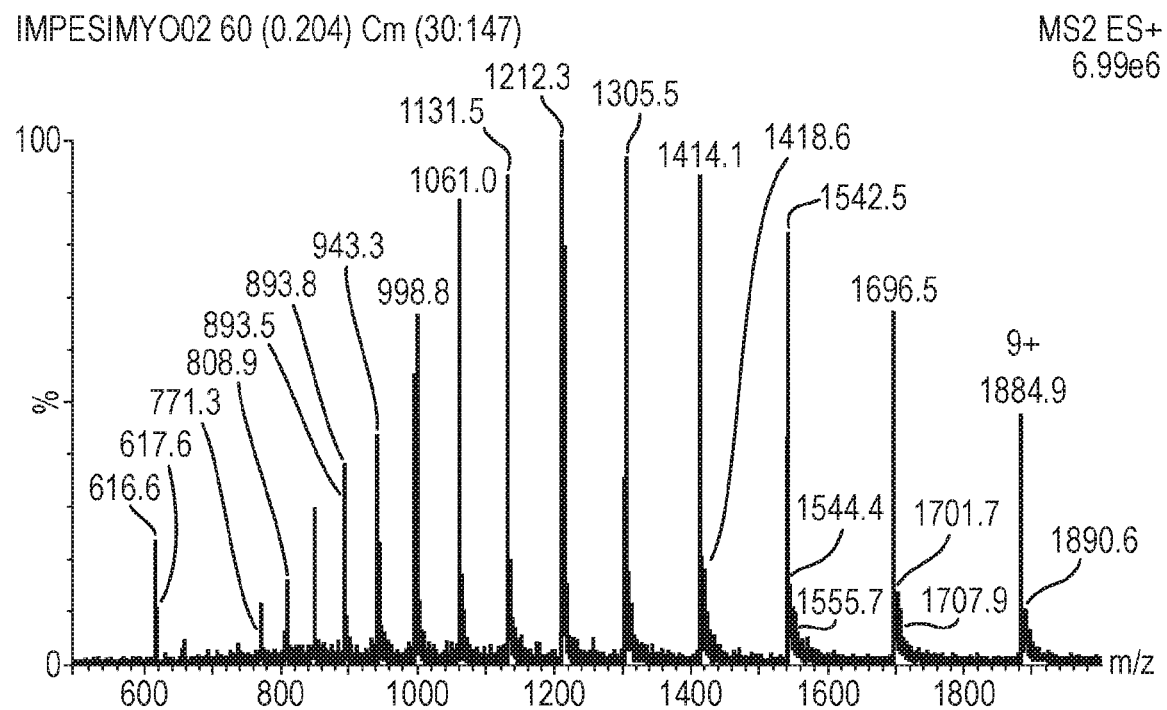
FIG. 6B shows a charge reduced mass spectrum obtained by critically tuning the point at which the spray from the Electrospray impact ionisation ion source strikes the target and FIG. 6C illustrates how the charge reduction increases as the impact point moves to the left of the point of maximum ion intensity.

FIGS. 6A and 6B illustrate charge reduction behaviour for the non-antibody protein sample Horse Heart Myoglobin ("HHM"). However, the beneficial effects of charge reduction of ions is equally achieved for monoclonal antibody ions and other biomolecules. In particular, it should be understood that various embodiments are contemplated wherein an Electrospray impact ionisation ion source may be utilised in order to analyse a monoclonal antibody sample (or other biomolecule sample) so that the resulting analyte ions are charge reduced.

FIG. 6A shows a mass spectrum for Horse Heart Myoglobin ("HHM") obtained by tuning an Electrospray impact ionisation ion source for maximum ion intensity. FIG. 6B shows a corresponding charge reduced spectrum which was obtained by critically tuning the point at which the spray from the Electrospray impact ionisation ion source struck the target or electrode.

Figure 6C:
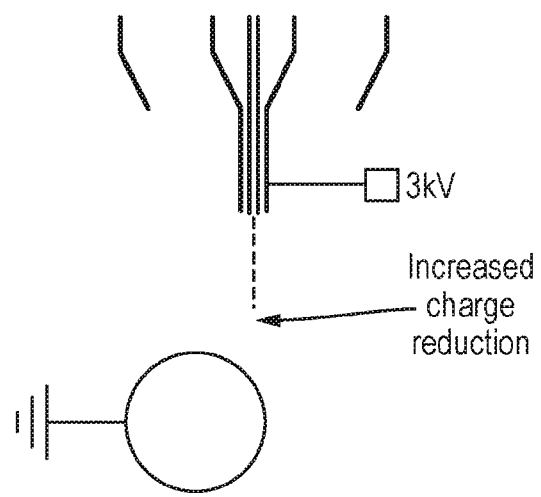

It is found that charge reduction increases as the impact point moves to the left of the point of maximum ion intensity as shown schematically in FIG. 6C. This tuning leads to an order of magnitude increase in the intensity of the 9+ ion which is observed in the mass spectrum. To highlight the critical nature of the tuning, it should be appreciated that the difference between the probe positions in FIG. 6A and FIG. 6B is approximately −150 μm.

LC/MS Analysis of Trastuzumab Monoclonal Antibody

The LC/MS method described above was repeated for the analysis of Trastuzumab monoclonal antibody using an Electrospray impact ionisation ion source that was tuned for (or otherwise optimised for) charge reduction. Prior to monoclonal antibody analysis, a cytochrome C solution was infused into the source at a flow rate of 0.2 mL/min and with a mobile phase composition of 1:1 water and acetonitrile (both with 0.1% formic acid). The sprayer position was tuned for high charge state reduction in a similar manner to the method described above in relation to the analysis of Horse Heart Myoglobin. Repeat injections of Trastuzumab were made on-column where the sprayer position was progressively moved in 25 μm steps between injections so that the intensity of the light chain ("LC") ion series (as indicated by the marker in FIG. 7A) was of the same intensity as the main intact ("I") monoclonal antibody ion series (as indicated by the marker ▲ in FIG. 7A).

Figure 7A:
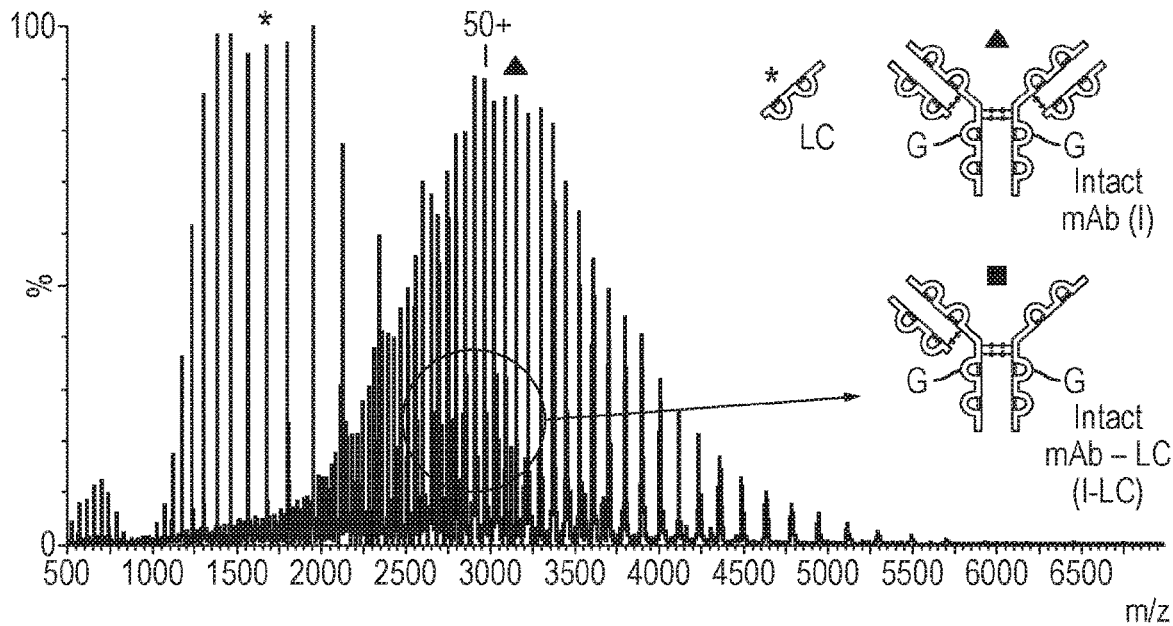
FIG. 7A shows a mass spectrum which was obtained wherein an Electrospray impact ionisation ion source was used to ionise a monoclonal antibody sample so as to produce light chain ("LC") ions and intact ("I") monoclonal antibody ions and FIG. 7B shows a mass spectrum for the mass range of 2700-3250 (as indicated by the circle in FIG. 7A) and reveals a hitherto unobserved ion series in the parent ion mass spectrum which is labelled with ■ markers and which corresponds with intact minus light chain ("I-LC") parent monoclonal antibody ions.

Referring to FIG. 7A, it will be seen from the mass spectrum shown in FIG. 7A that the Electrospray impact ionisation ion source produces both light chain ("LC") and intact ("I") monoclonal antibody ions. The centre of the intact distribution is shifted by typically 7 charge states when compared with a corresponding Electrospray ionisation ("ESI") mass spectrum as shown in FIG. 5A. The mass range 2700-3250 is highlighted in FIG. 7A and is shown in more detail in FIG. 7B.

Figure 7B:
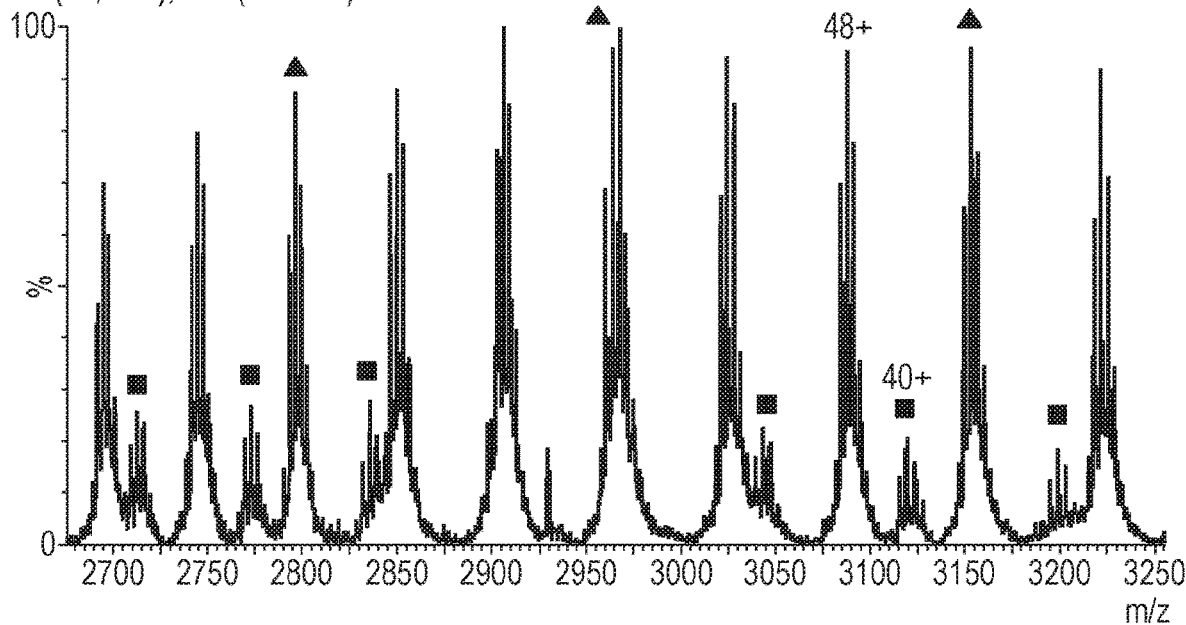

With reference to FIG. 7B, when the mass spectral data is observed in high resolution then it is apparent that a previously unobserved ion series is also observed as labelled with ■ markers. The newly observed ion series corresponds to intact Trastuzumab ions which have lost a light chain ("I-LC") presumably by cleavage of the disulphide bridges.

FIG. 7A summarizes the ion schemes produced by the Electrospray impact ionisation ion source according to various embodiments namely the production of light chain ("LC") fragment monoclonal antibody ions, intact ("I") parent monoclonal antibody ions and intact minus light chain ("I-LC") parent monoclonal antibody ions.

The newly observed intact minus light chain ("I-LC") parent monoclonal antibody ions have not been observed using either Collision Induced Dissociation ("CID") or Electron Transfer Dissociation ("ETD") fragmentation techniques or by post column addition of charge reduction agents. The newly observed intact minus light chain ("I-LC") parent ions are also not observed when operating an Electrospray ionisation ("ESI") ion source within conventional operational conditions.

The production of (and ability to recognise the presence of) intact minus light chain ("I-LC") parent monoclonal antibody ions enables enhanced capabilities for biopharmaceutical quality control through an additional critical quality attribute ("CQA") monitoring.

In order to determine whether the novel intact minus light chain ("I-LC") fragmentation pathway was generic to monoclonal antibody analysis, the current LC/MS method was repeated using a number of different commercially available monoclonal antibody standards.

Testing with Different Monoclonal Antibody Standards

Figure 8:
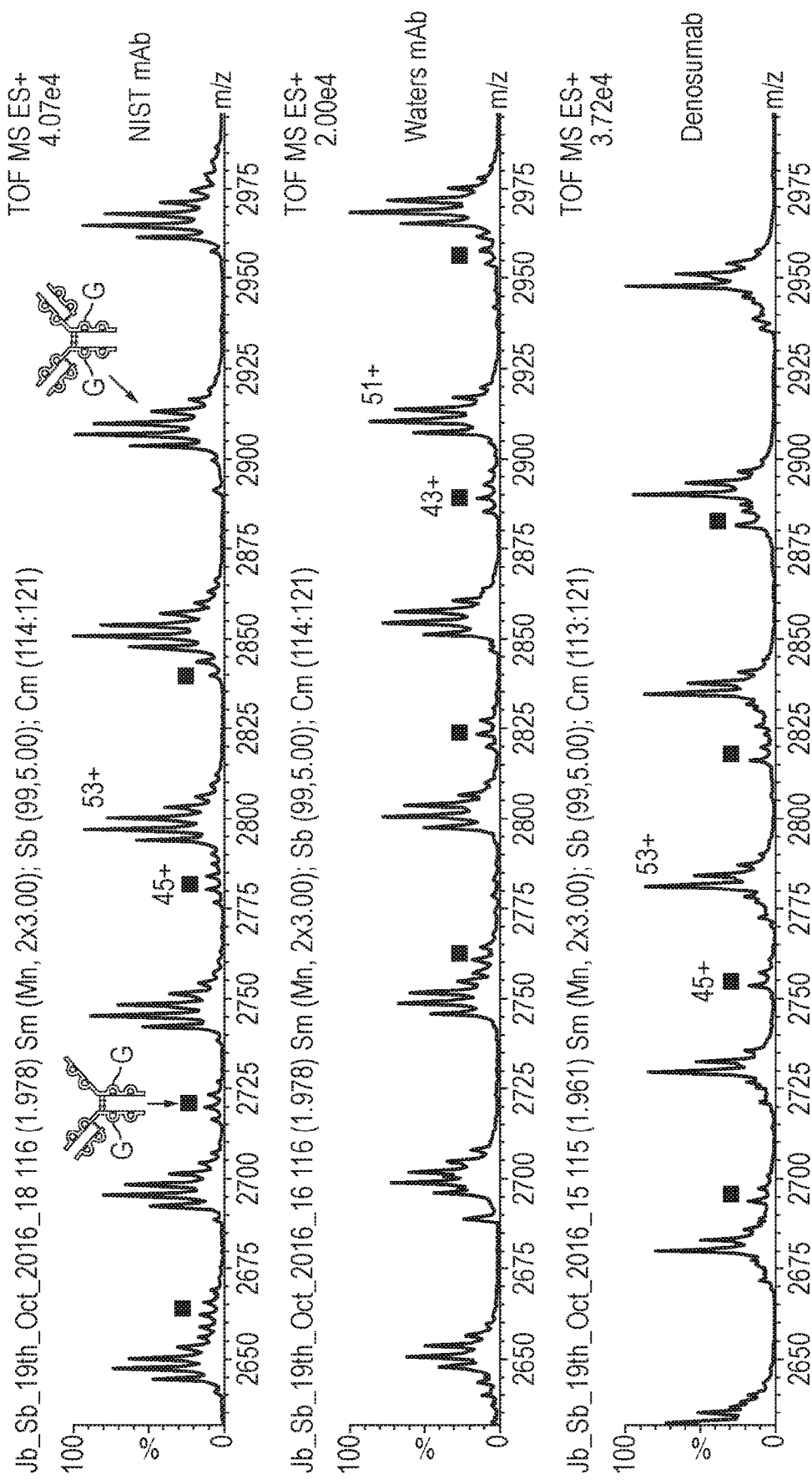
FIG. 8 shows mass spectra obtained for different monoclonal antibody standards namely a NIST monoclonal antibody standard, a Waters® monoclonal antibody standard and a Denosumab monoclonal antibody standard, wherein the mass spectra were obtained using an Electrospray impact ionisation ion source and wherein the same distinctive intact minus light chain ("I-LC") parent monoclonal antibody ions are obtained for each monoclonal antibody standard sample as indicated by ■ markers.

FIG. 8 shows mass spectra obtained for NIST monoclonal antibody, Waters® monoclonal antibody and Denosumab standards using an Electrospray impact ionisation ion source. It is apparent that the same characteristic intact minus light chain ("I-LC") parent monoclonal antibody ions are obtained for each standard monoclonal antibody sample. The intact minus light chain ions are labelled with ■ markers in FIG. 8.

Figure 9:
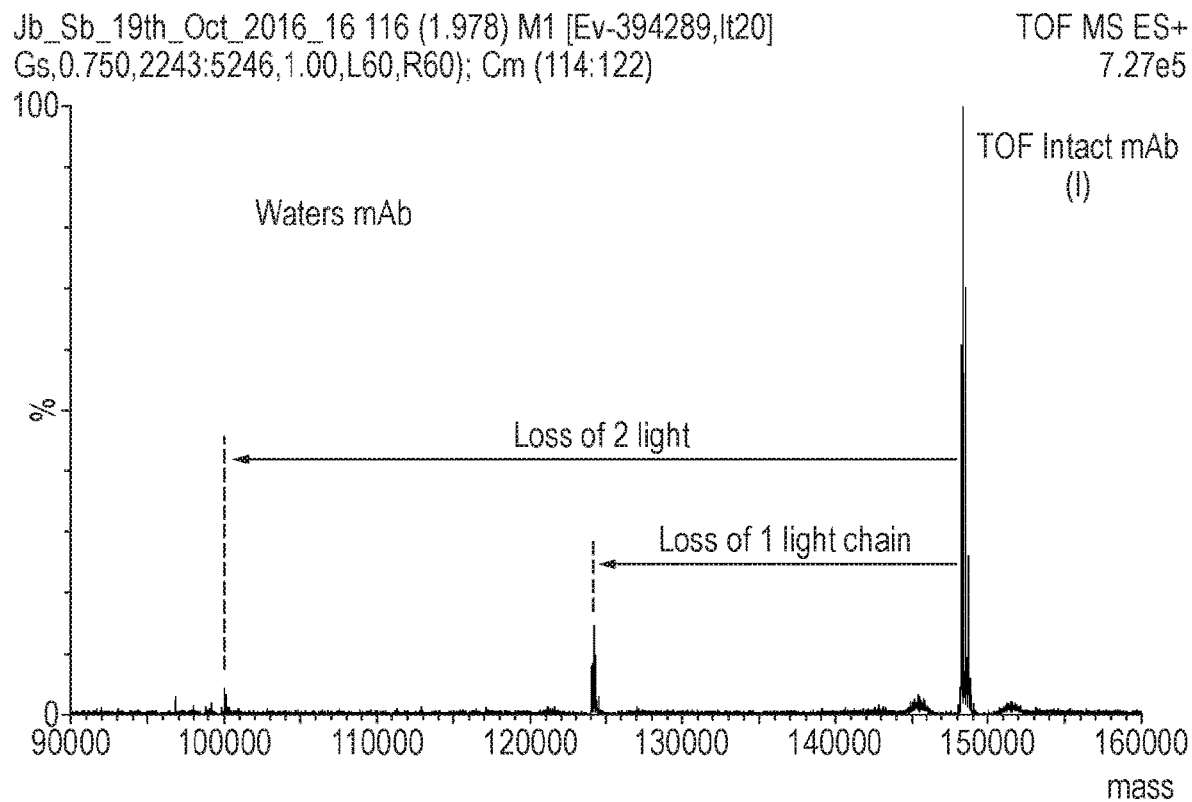
FIG. 9 shows a transformed mass spectrum for data relating to the analysis of a Waters® monoclonal antibody standard on a true mass scale (charge state=0) which confirms that the nominal loss of 24198 Da from the intact monoclonal antibody is due to the loss of a light chain ("LC")

FIG. 9 shows a transformed mass spectrum for the Waters® monoclonal antibody data on a true mass scale (charge state=0) which confirms that the nominal loss of 24198 Da from the intact monoclonal antibody is due to the loss of the light chain. It is observed that the intact minus light chain ("I-LC") ions have a typical +10 Da mass excess which may be due to a systematic mass accuracy error or possibly reduction of one or more disulphide bridges in the fragment ion. This data also shows that both light chains may be lost from the monoclonal antibody by this process.

In contrast to the mass spectra which were obtained according to various embodiments and which have been described above with reference to FIGS. 8 and 9, the conventional mass spectrum shown in FIG. 5A shows that intact minus light chain ("I-LC") parent monoclonal antibody ions are not observed under conventional Electrospray ionisation ("ESI") operating conditions wherein the capillary voltage is maintained at around 3 kV and the capillary/ion inlet distance is typically 10 mm.

Gap Electrospray ("G-ESI") Ion Source

A modified Electrospray ionisation ("ESI") ion source will now be discussed in more detail below which enables both intact minus light chain ("I-LC") parent monoclonal antibody ions and light chain ("LC") fragment monoclonal antibody ions to be generated.

Figure 10:
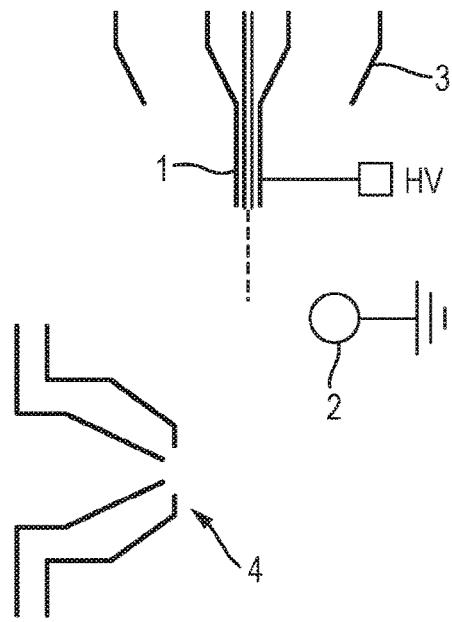
FIG. 10 shows a schematic of a new type of ion source according to various embodiments which is referred to hereinafter as a Gap Electrospray ("G-ESI") ion source wherein the capillary voltage of an Electrospray ion source is increased from 3.5 kV to a voltage in the range 4-5 kV and wherein the Electrospray ionisation probe is positioned such that the spray plume which emerges from the probe traverses a gap between a target or electrode and an ion inlet cone of a mass spectrometer.

FIG. 10 shows a schematic of the new form of Electrospray ion source which will be referred to hereinafter as a Gap Electrospray ("G-ESI") ion source. According to this embodiment the capillary voltage of an Electrospray impact ion source is increased from a conventional voltage of up to 3.5 kV to a higher than conventional voltage in the range 4-5 kV. The Electrospray ionisation ("ESI") probe 1 is also positioned such that the spray plume emitted from the probe 1 traverses the gap between the target or electrode 2 and the ion inlet cone 4 of a mass spectrometer. As far as plume impact is concerned, the target or electrode 2 is now completely passive i.e. charged droplets emitted from the probe 1 do not substantially impact the electrode 2. However, the target or electrode 2 influences the shape and magnitude of the gap field in this region. This high voltage gap arrangement may result in visible discharges between the capillary and the target or electrode 2. However, such discharges may be arrested by the use of a 1 MΩ current-limiting resistor.

By way of contrast, a conventional Electrospray impact ionisation ion source as shown in FIG. 2 with a capillary voltage of up to 3.5 kV operates under stable conditions with a significantly lower gap current and no visible discharges.

Figure 11A:
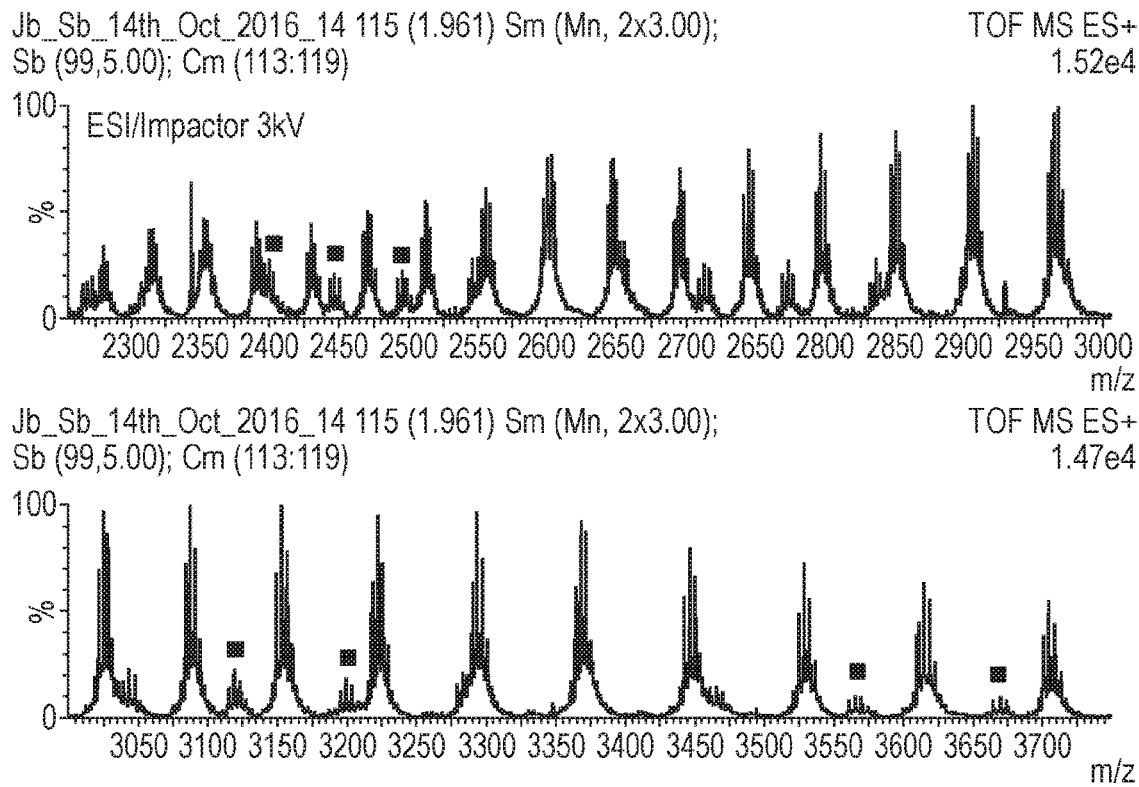
FIG. 11A shows mass spectra according to various embodiments which was obtained utilising an Electrospray impact ionisation ion source wherein the capillary voltage was maintained at 3.5 kV and was operated under stable conditions with a significantly lower gap current and no visible discharges
Figure 11B:
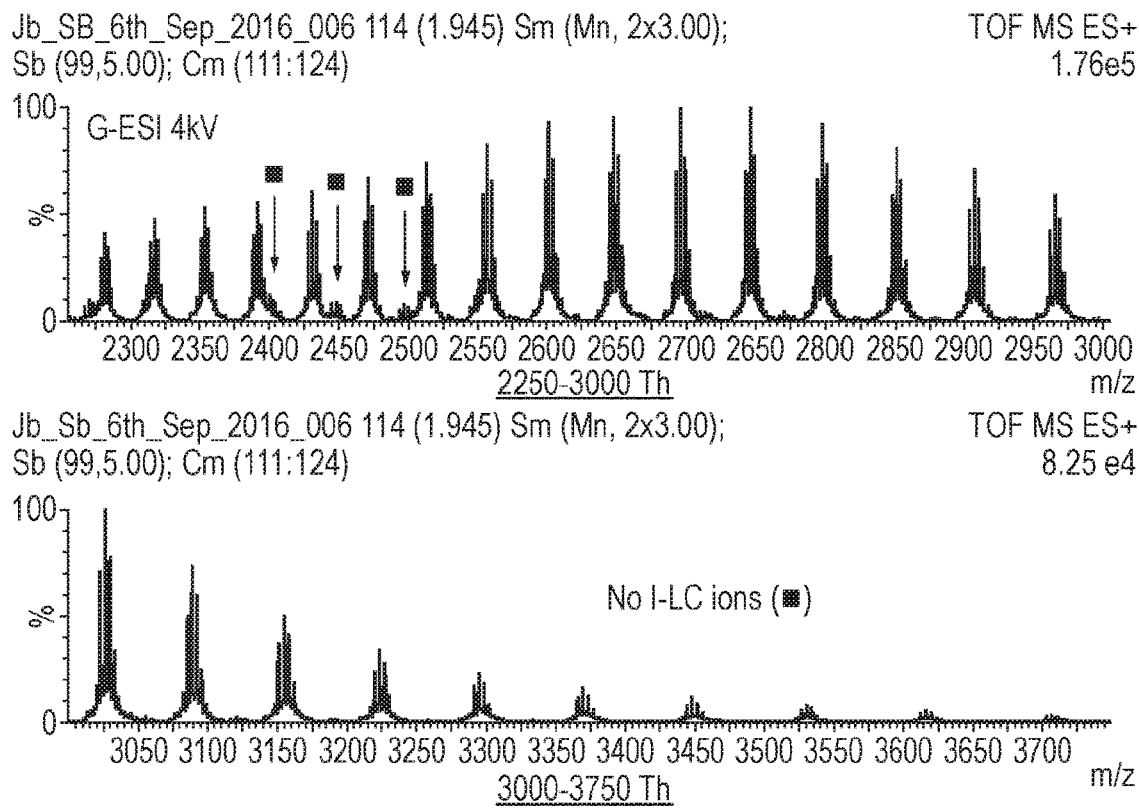
FIG. 11B shows corresponding mass spectra obtained utilising a Gap Electrospray ("G-ESI") ion source according to various embodiments.

FIG. 11A shows a Trastuzumab antibody mass spectrum obtained using an Electrospray impact ionisation ion source and FIG. 11B shows a corresponding mass spectrum obtained using a Gap Electrospray ion source according to various embodiments. The Gap Electrospray ion source is shown to produce intact minus light chain ("I-LC") parent monoclonal antibody ions over a limited m/z range (<2600 Da) as indicated by the markers ■ whilst the mass spectrum relating to the Electrospray impact ionisation ion source as shown in FIG. 11A shows a clear intact minus light chain ("I-LC") parent monoclonal antibody ion series as shown by the marker ■ over the whole shown mass range.

It can be demonstrated that a visibly discharging Electrospray ionisation probe can also produce intact minus light chain ("I-LC") parent monoclonal antibody ions as is shown in FIG. 11B. The ability to produce multiply charged ion series over a wide m/z range will greatly improve the mass accuracy of algorithms that transform mass spectra from the m/z scale to a true mass scale. Furthermore, the ability to charge reduce the ion series to higher m/z values is important for real biological samples since the higher m/z regions tend to contain significantly reduced background ion contamination which further increases spectral quality and mass accuracy of transformed data.

Although it is has been shown that intact minus light chain ("I-LC") ions can be obtained from Electrospray ionisation ion sources that are subjected to electrical discharges, there is no evidence to suggest that the discharge alone can lead to significant charge reduction of the multiply charged monoclonal antibody ions. Rather, this charge reduction process requires the direct use of a surface or electrode as is the case in an Electrospray impact ionisation ion source. Although not fully understood, it is likely that both the stable gap current and the critical impact conditions at the target or electrode surface play an important role in the ionisation and charge reduction mechanisms pertaining to an Electrospray impact ionisation source.

Alternatives

Although the various embodiments disclosed above are focused upon the analysis of monoclonal antibodies, the apparatus and methods disclosed in the present application are also applicable to a wide range of biomolecules and other biotherapeutics and not just monoclonal antibodies.

It is known to operate a conventional Electrospray ionisation ("ESI") ion source at high voltages (5-10 kV) in order to induce breakdown wherein oxygen gas is then added to the source in order to study oxidation of proteins or the binding of protein complexes. For example, reference is made to an Electrospray ionisation ("ESI") ion source for protein analysis as disclosed in Anal. Chem. 2003, 75, 1557-1563. Such an approach may also be adopted with the apparatus and methods according to various embodiments as disclosed in the present application.

With reference to known discharging Electrospray ionisation ("ESI") sources, it will be understood by those skilled in the art that energetic visible discharges are hard to replicate and can vary from one instrument to the other depending on the state of various components and other parameters such as surface cleanliness, etc. In addition, the nature of the discharge may change with time due to degradation of the discharge components. These effects will hamper the reproducibility of analyses conducted on such instrumentation.

Although reference has been made throughout the present application to intact minus light chain ("I-LC") ions as comprising (essentially) parent monoclonal antibody ions, it is recognised that intact minus light chain ("I-LC") ions might also or alternatively be considered to comprise fragment monoclonal antibody ions. Accordingly, any reference in the present application to intact minus light chain ("I-LC") parent monoclonal antibody ions should also be taken to mean intact minus light chain ("I-LC") ions fragment monoclonal antibody ions.

Ionisation of Bovine Insulin

Collision-induced dissociation ("CID") is a known technique that may be used in mass spectrometry ("MS") to fragment ions prior to their mass analysis. In this technique, analyte ions are selected by a mass filter and then accelerated into a gas cell at energies of typically <100 eV. The gas cell may be filled with argon collision gas at a pressure of approximately $10^{-3}$ mbar. The method of generating fragment ions from a selected precursor is generally referred to as MS/MS. The resulting fragment ions may be used for structural elucidation in the case of unknown analytes or for structural confirmation in the case of target analytes.

Ions of small molecules tend to fragment at multiple bond positions which give rise to mass spectra that are rich in structural information. On the other hand, large biomolecular ions have many energy-absorbing degrees of freedom and tend to produce only a small number of large fragments that are associated with the most labile bond positions within the "macrostructure" or backbone of the molecule when fragmented by this method.

This CID limitation is even more pronounced in the case of large "compact" or folded, biomolecular ions, such as those that contain multiple disulphide bridges which are commonly referred to as S—S bonds. Since these bonds drastically reduce the effectiveness of CID, it is common for analysts to use alternative or complimentary techniques such as chemical reduction, electron capture dissociation ("ECD") or electrochemical cell technology. In the case of chemical reduction, the S—S bonds are cleaved in solution by adding a reducing agent such as dithiothreitol ("DTT") to the sample prior to CID/MS/MS analysis.

Atmospheric pressure ECD in combination with CID has also been shown to increase the number of fragments in the MS analysis of biomolecules. Additionally, the use of an electrochemical cell to reduce the S—S bonds prior to electrospraying the sample can also be used in combination with CID/MS/MS to enhance structural information. Although these methods have been used with some success, they add significant complexity to both the analytical method and the MS instrumentation. It is desired to have a facile method of obtaining high-coverage structural information from complex biomolecules that is based on common MS instrumentation.

As detailed above, it has been shown that in-source fragmentation of a monoclonal antibody (mAb) can occur in an Electrospray impact ionisation ion source where the loss of the mAb light chain is observed due to reduction of the disulphide (S—S) bond that links the light and heavy chains.

It has been shown that the in-source reduction process observed with an Electrospray impact ionisation ion source is far more efficient when compared to a conventional Electrospray ionisation ion source. An analytical method for the enhanced fragmentation of biomolecules that utilizes an Electrospray ionisation ion source in combination with ion mobility/CID/MS/MS will now be described below in more detail.

Impact Ionisation and Electrospray Impact Ionisation Ion Sources

Figure 12A:
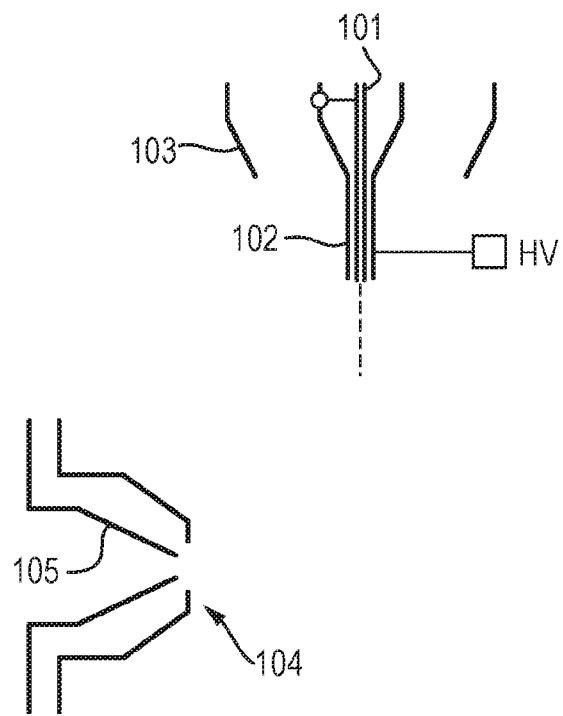
FIG. 12A shows a known Electrospray ionisation ("ESI") ion source.
Figure 12B:
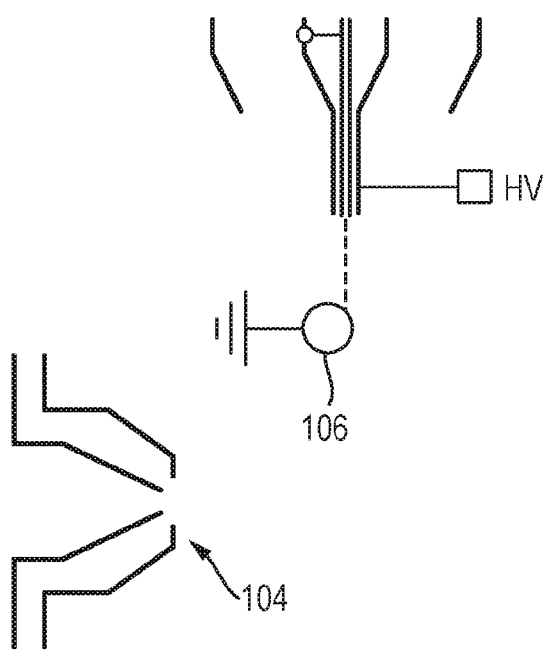
FIG. 12B shows an Electrospray impact ionisation ion source and FIG. 12C shows a type of ion source according to various embodiments which is referred to as a Gap Electrospray ("G-ESI") ion source.
Figure 12C:
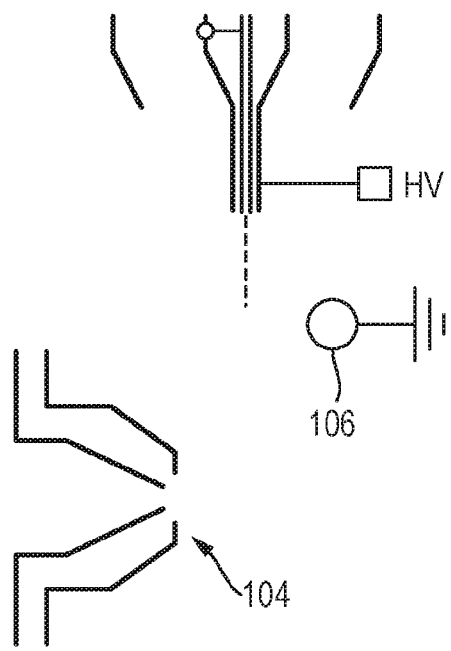

FIGS. 12A, 12B, and 12C show ionisation source types that may be used for the ionisation of biomolecules. All three may utilise a pneumatically-assisted ESI probe design. A known Electrospray ionisation ion source shown in FIG. 12A includes an Electrospray probe comprising a liquid capillary 101 and an outer gas capillary 102. In one arrangement the inner liquid capillary 101 is an inner stainless steel liquid capillary 101, which may have dimensions 130 μm i.d.×220 μm o.d. and the outer liquid capillary 102 is an outer, concentric, stainless steel gas capillary 102, which may have dimensions 330 μm i.d.×440 μm o.d. In use, a solution containing the biomolecular sample may be passed through the probe at flow rates of typically 0.005-1 mL/min. In one arrangement the gas capillary inlet may be pressurised to 7 bar which creates a high-velocity jet with a typical flow rate of about 120 L/hr at the probe exit. This gas flow may beneficially aid nebulization of the liquid flow.

In order to aid charging of the spray plume, the inner and outer capillaries 101,102 are electrically connected and are held at a potential with respect to an ion inlet cone 105, that may be +3-4 kV with respect to the ion inlet cone 105 for positive ion analysis. Desolvation of the spray plume may be aided by a concentric flow of hot nitrogen gas which may be provided from the desolvation heater 103 and which may be provided at 200-350° C. and at a flow rate of 1000 L/hr. Ions created in the electrospray are sampled into the MS through an ion inlet orifice 104, which may measure 0.4-0.8 mm in diameter. The inlet orifice 104 creates a boundary between the atmospheric pressure region of the source and the first vacuum region of the MS.

FIG. 12B shows an Electrospray impact ionisation ion source which includes an Electrospray probe that may be the same as that shown in FIG. 12A, and further includes an ion inlet orifice and an ion inlet cone both of which may also be the same as those shown in FIG. 12A. A target 106 is also provided, that in one arrangement may be a cylindrical, grounded metallic target 106 with a diameter of 1.6 mm, such that the spray plume impacts on the upper right-hand quadrant of the cylindrical grounded metallic target 106. The target 106 may be arranged so as to be off-axis, such that the gas flow becomes attached to the curved surface of the target 106 and the wake flow is directed towards the ion inlet orifice 104. In one arrangement the target 106 may be positioned 5 mm in front of and 10 mm above the ion inlet orifice 104.

FIG. 12C shows a Gap Electrospray ionisation ion source which in terms of geometrical arrangement is similar to the impact ionisation source as shown in FIG. 12B except that although the target 106 may be positioned close to the ESI plume, the plume does not impact on the target 106. In one arrangement the grounded target may be positioned close i.e. approx. 3-4 mm from the plume. Although similar to a conventional Electrospray ionisation ion source, the presence of the target 106 can significantly influence the electrical discharge characteristics of the source since its surface becomes the closest ground point and hence an important electric field shaping component.

In the arrangements shown in FIGS. 12A, 12B and 12C the probe position may be adjustable in the x and y directions (i.e. in the plane of the page) and all of the ion source types may operate at atmospheric pressure. In some arrangements the ion sources may be surrounded by an air tight enclosure that may include an exhaust outlet to vent to gasses and vapour.

Figure 13:
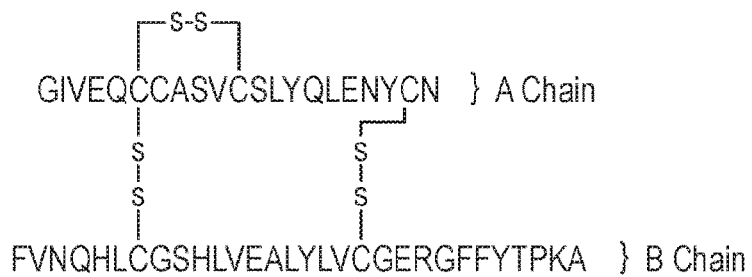
FIG. 13 shows a schematic of the structure of a bovine insulin molecule.

Bovine insulin is a two-chain polypeptide hormone where the A and B chains are connected via two S—S bonds as shown schematically in FIG. 13. Large biomolecules such as bovine insulin (MW=5729.60 Da) are not generally amenable to CID/MS/MS analysis without the use of sample preparation or alternative S—S bond reduction techniques.

Although various known methods of obtaining structural information from biomolecule fragments and fragment ions increase the ability to characterise biomolecules, such methods are problematic in that they are comparatively complex. Furthermore these may require the provision of, for example, an electrochemical cell.

In contrast to the known methods, methods according to various embodiments are disclosed below which are particularly advantageous in that they enable complex biomolecule fragment ions, such as bovine insulin fragment ions, to be produced via a simple process which does not involve either an electrochemical cell or a chemical reduction method.

It will be understood, therefore, by those skilled in the art that the ability to straightforwardly and simply produce, recognise and analyse both parent intact bovine insulin ions and associated fragment bovine insulin ions represents a significant advance in the art. Also, it should be understood that more generally the ability to straightforwardly and simply produce, recognise and analyse biomolecules having one or more disulphide bonds represents a significant advance in the art It is known to use impact ionisation ion sources which involve generating a beam of droplets which are emitted from a pneumatic nebuliser. The beam of droplets is caused to impact upon a closely positioned target plate or cylindrical rod.

According to various embodiments which will be described in more detail below a conventional impact ionisation ion source, an Electrospray impact ionisation ion source and a Gap Electrospray ionisation ion source may be used to obtain mass spectral data directly from a sample of bovine insulin (or other biomolecules having one or more disulphide bonds). The bovine insulin (or other biomolecule) may be eluting from a liquid chromatography separation device. The mass spectral data which is obtainable according to various embodiments shows new additional structural information relating to bovine insulin analytes which is of particular interest and which is either not obtainable or which is at least not easily obtainable using conventional methods.

FIG. 13 shows a schematic of the structure of a bovine insulin molecule which has a molecular weight of ~5729.60 Da. The bovine insulin molecule is a two-chain polypeptide hormone where A and B chains are connected via two S—S bonds.

Analysis of Bovine Insulin

Various embodiments will now be described with reference to the apparatus shown in FIG. 12A, FIG. 12B, and FIG. 12C. According to various embodiments an Electrospray impact ionisation ion source and the Gap Electrospray ionisation ion source were both used to analyse a bovine insulin sample. 5 pmol/μL bovine insulin solution was prepared in 1:1 methanol:water with 1% acetic acid. This solution was infused at 10 μl/min into a 0.4 mL/min make-up flow of 1:1 acetonitrile:water containing 0.1% formic acid and the resulting flow was introduced into an Electrospray impact ionisation ion source or a Gap Electrospray ionisation ion source for MS analysis. The probe voltage was set at 3 kV.

Figure 14A:
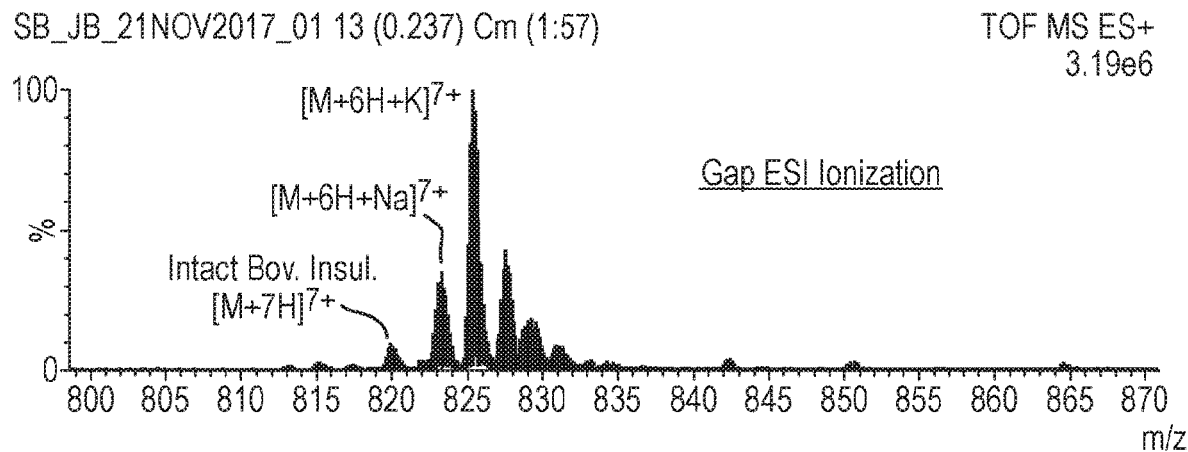
FIG. 14A shows a mass spectrum obtained according to various embodiments using a Gap Electrospray ion source to ionise a bovine insulin sample to produce intact bovine insulin ions and other common salt adducts and FIG. 14B shows a mass spectrum obtained according to various embodiments wherein an Electrospray impact ionisation ion source was used to ionise a bovine insulin sample to produce the same intact bovine insulin series as FIG. 14A as well as a relatively stronger signal for the bovine insulin B chain ion, wherein the Electrospray impact ionisation data of FIG. 14B was obtained with a cylindrical aluminium target (diameter 1.6 mm) which gives greater B chain ion intensities than observed with a conventional stainless steel target.
Figure 14B:
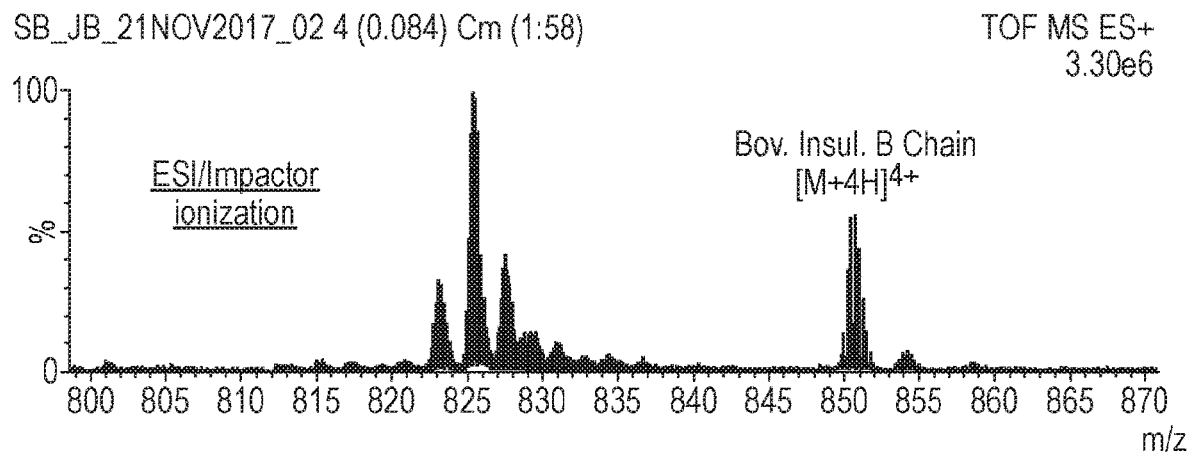

As shown in FIG. 14A, the Gap Electrospray ionisation ion source produces intact bovine insulin ions [M+7H]$^{7+}$ and other common salt adducts. The usual distribution of lower charge states of intact bovine insulin were also observed but are not shown here. In comparison, FIG. 14B shows that the Electrospray impact ionisation ion source produces the same intact bovine insulin ion series but also produces a relatively strong signal for the bovine insulin B chain ion ([M+4H]$^{4+}$). A weaker [M+5]$^{5+}$ B chain ion was also observed (not shown).

By comparison with the observation of S—S bond reduction of mAbs described above, it will be apparent from comparing FIG. 14A with FIG. 14B that the Electrospray impact ionisation ion source promotes reduction and in-source cleavage of the two S—S bonds between the A and B chains shown in FIG. 13.

It will also be apparent from FIG. 14A that a small amount of B chain ion is also produced by the Gap Electrospray ionisation ion source.

Both the spectra shown in FIGS. 14A and 14B were obtained with a probe voltage of 3 kV.

Accordingly, the method according to various embodiments enables a certain multiply-charged ion fragment species ("B") of bovine insulin molecules to be easily and readily observed without requiring complex and time consuming sample preparation steps to be performed and/or without requiring alternative or complimentary techniques such as chemical reduction, electron capture dissociation ("ECD") or electrochemical cell technology.

The various embodiments therefore are particularly advantageous in that the approach according to various embodiments enables the B chain ion component of bovine insulin molecules to be readily observed by simply ionising a sample of bovine insulin without requiring complex and time consuming sample preparation steps to be performed and/or without needing to subject the sample to alternative or complimentary techniques such as chemical reduction, electron capture dissociation ("ECD") or electrochemical cell technology.

It is typically found that, while in the case of the Electrospray impact ionisation ion source a relatively strong B chain ion signal may be observed before the onset of a visible electrical discharge at the probe tip whilst B chain ions may only be observed with the Gap Electrospray ionisation ion source under conditions of a visible discharge. Further, a conventional Electrospray ionisation ion source, as shown in FIG. 12A, may produce a weak B chain ion signal but only under conditions of a visible discharge which would only occur at high applied voltages such as ~5 kV.

As such although the three source types may all promote in source reduction of S—S bonds to some degree, it is clear that an Electrospray impact ionisation ion source is beneficial in terms of ion intensities. Further, it is also noted that the Electrospray impact ionisation ion source data shown in FIG. 14B was obtained with a cylindrical aluminium target (Ø1.6 mm) which gave greater B chain ion intensities than observed with a conventional stainless steel target.

A particularly advantageous aspect of the various disclosed embodiments is, therefore, that by using an Electrospray impact ionisation ion source it is possible to reveal additional structural information (e.g. observe B chain ions) in a simple and straightforward process wherein such B chain ions are not observed using a conventional Electrospray ionisation ("ESI") source (unless bovine insulin molecules are subjected to a prior cleaving step by chemical reduction).

Impact Ionisation and Electrospray Impact Ion Ionisation Ion Sources

According to an embodiment an Electrospray impact ionisation ion source may be utilised wherein the ion source is electrically biased with a high voltage applied to the pneumatic sprayer and a grounded target similar to the Electrospray impact ionisation ion source as shown and described above with reference to FIG. 12B.

An impact ionisation ion source and an Electrospray impact ionisation ion source as may be used according to various embodiments may comprise one or more nebulisers and one or more targets or electrodes. The one or more nebulisers may be arranged and adapted to emit, in use, a stream predominantly of droplets which are caused to impact upon the one or more targets or electrodes and to ionise the droplets so as to form a plurality of ions.

The droplets may comprise analyte droplets and the plurality of ions may comprise analyte ions. However, it is also contemplated that the droplets may comprise reagent droplets and the plurality of ions may comprise reagent ions. It is contemplated that any reagent ions which are created may react, interact with or transfer charge to neutral analyte molecules and cause the analyte molecules to become ionised. Reagent ions may also be used to enhance the formation of analyte ions.

Embodiments are contemplated wherein one or more tubes may be arranged and adapted to supply analyte(s) or other gases to a region adjacent the one or more targets or electrodes. Reagent ions may be arranged so as to ionise analyte gas so as to form a plurality of analyte ions.

An analyte liquid may be supplied to the one or more targets or electrodes and may be ionised to form a plurality of analyte ions and/or a reagent liquid may be supplied to the one or more targets or electrodes and may be ionised to form reagent ions which transfer charge to neutral analyte atoms or molecules to form analyte ions and/or which enhance the formation of analyte ions.

The one or more targets or electrodes may have one or more apertures and the analyte liquid and/or reagent liquid may be supplied directly to the one or more targets or electrodes. The liquid may be arranged so as to emerge from the one or more apertures. It is also contemplated that the one or more targets or electrodes may be coated with one or more liquid, solid or gelatinous analytes so that the one or more analytes are ionised so as to form a plurality of analyte ions. For example, it is contemplated that a bovine insulin sample may be coated on to a target plate or target cylinder and that the bovine insulin sample is that analysed by directing droplets from an impact ionisation ion source on to the target plate, target cylinder or electrode. It is also contemplated that the one or more targets or electrodes may be formed from one or more analytes and that the one or more analytes may be ionised to form a plurality of analyte ions.

The ion source which is used according to various embodiments may comprise an Atmospheric Pressure Ionisation ("API") ion source.

If an impact ionisation ion source is utilised then the one or more nebulisers may be arranged and adapted such that the majority of the mass or matter emitted by the one or more nebulisers is in the form of droplets not vapour. For example, at least 50%, 55%, 60%, 65%, 70%, 75%, 80%, 85%, 90% or 95% of the mass or matter emitted by the one or more nebulisers may be in the form of droplets. The one or more nebulisers may be arranged and adapted to emit a stream of droplets wherein the Sauter mean diameter ("SMD", d32) of the droplets is in a range: (i) <5 µm; (ii) 5-10 µm; (iii) 10-15

μm; (iv) 15-20 μm; (v) 20-25 μm; or (vi) >25 μm. The stream of droplets emitted from the one or more nebulisers may form a stream of secondary droplets after impacting the one or more targets or electrodes. The stream of droplets and/or the stream of secondary droplets may traverse a flow region with a Reynolds number (Re) in the range: (i) <2000; (ii) 2000-2500; (iii) 2500-3000; (iv) 3000-3500; (v) 3500-4000; or (vi) >4000. At the point of the droplets impacting the one or more targets or electrodes the droplets may have a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000. At the point of the droplets impacting the one or more targets or electrodes the droplets may have a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50. The mean axial impact velocity of the droplets upon the one or more targets or electrodes may be selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s. The one or more targets or electrodes may be arranged <20 mm, <19 mm, <18 mm, <17 mm, <16 mm, <15 mm, <14 mm, <13 mm, <12 mm, <11 mm, <10 mm, <9 mm, <8 mm, <7 mm, <6 mm, <5 mm, <4 mm, <3 mm or <2 mm from the exit of the one or more nebulisers.

The one or more nebulisers may be arranged and adapted to nebulise one or more eluents emitted by one or more devices over a period of time. The one or more devices may comprise one or more liquid chromatography separation devices. The one or more nebulisers may be arranged and adapted to nebulise one or more eluents, wherein the one or more eluents have a liquid flow rate selected from the group consisting of: (i) <1 (ii) 1-10 (iii) 10-50 μL/min; (iv) 50-100 μL/min; (v) 100-200 μL/min; (vi) 200-300 μL/min; (vii) 300-400 μL/min; (viii) 400-500 μL/min; (ix) 500-600 μL/min; (x) 600-700 μL/min; (xi) 700-800 μL/min; (xii) 800-900 μL/min; (xiii) 900-1000 μL/min; (xiv) 1000-1500 μL/min; (xv) 1500-2000 μL/min; (xvi) 2000-2500 μL/min; and (xvii) >2500 μL/min. The one or more nebulisers may according to other embodiments comprise one or more rotating disc nebulisers.

The one or more nebulisers may comprise a first capillary tube having an exit which emits, in use, the stream of droplets. The first capillary tube may maintained, in use, at a potential: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV.

The first capillary tube may be maintained, in use, at a potential of: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV; relative to the potential of an enclosure surrounding the ion source and/or an ion inlet device which leads to a first vacuum stage of a mass spectrometer and/or the one or more targets.

According to an embodiment a wire may be located within the volume enclosed by the first capillary tube wherein the wire is arranged and adapted to focus the stream of droplets. The first capillary tube may be surrounded by a second capillary tube which is arranged and adapted to provide a stream of gas to the exit of the first capillary tube. Alternatively, the second capillary tube may be arranged and adapted to provide a cross flow stream of gas to the exit of the first capillary tube. The second capillary tube may surround the first capillary tube and/or may be either concentric or non-concentric with the first capillary tube. The ends of the first and second capillary tubes may be either: (i) flush or parallel with each other; or (ii) protruded, recessed or non-parallel relative to each other.

The exit of the first capillary tube may have a diameter D and the spray of droplets may be arranged to impact on an impact zone of the one or more targets or electrodes. The impact zone may have a maximum dimension of x and wherein the ratio x/D is in the range <2, 2-5, 5-10, 10-15, 15-20, 20-25, 25-30, 30-35, 35-40 or >40. The impact zone may have an area selected from the group consisting of: (i) <0.01 $mm^2$; (ii) 0.01-0.10 $mm^2$; (iii) 0.10-0.20 $mm^2$; (iv) 0.20-0.30 $mm^2$; (v) 0.30-0.40 $mm^2$; (vi) 0.40-0.50 $mm^2$; (vii) 0.50-0.60 $mm^2$; (viii) 0.60-0.70 $mm^2$; (ix) 0.70-0.80 $mm^2$; (x) 0.80-0.90 $mm^2$; (xi) 0.90-1.00 $mm^2$; (xii) 1.00-1.10 $mm^2$; (xiii) 1.10-1.20 $mm^2$; (xiv) 1.20-1.30 $mm^2$; (xv) 1.30-1.40 $mm^2$; (xvi) 1.40-1.50 $mm^2$; (xvii) 1.50-1.60 $mm^2$; (xviii) 1.60-1.70 $mm^2$; (xix) 1.70-1.80 $mm^2$; (xx) 1.80-1.90 $mm^2$; (xxi) 1.90-2.00 $mm^2$; (xxii) 2.00-2.10 $mm^2$; (xxiii) 2.10-2.20 $mm^2$; (xxiv) 2.20-2.30 $mm^2$; (xxv) 2.30-2.40 $mm^2$; (xxvi) 2.40-2.50 $mm^2$; (xxvii) 2.50-2.60 $mm^2$; (xxviii) 2.60-2.70 $mm^2$; (xxix) 2.70-2.80 $mm^2$; (xxx) 2.80-2.90 $mm^2$; (xxxi) 2.90-3.00 $mm^2$; (xxxii) 3.00-3.10 $mm^2$; (xxxiii) 3.10-3.20 $mm^2$; (xxxiv) 3.20-3.30 $mm^2$; (xxxv) 3.30-3.40 $mm^2$; (xxxvi) 3.40-3.50 $mm^2$; (xxxvii) 3.50-3.60 $mm^2$; (xxxviii) 3.60-3.70 $mm^2$; (xxxix) 3.70-3.80 $mm^2$; (xl) 3.80-3.90 $mm^2$; and (xli) 3.90-4.00 $mm^2$.

The ion source may further comprise one or more heaters which are arranged and adapted to supply one or more heated streams of gas to the exit of the one or more nebulisers. The one or more heaters may surround the first capillary tube and may be arranged and adapted to supply a heated stream of gas to the exit of the first capillary tube. The one or more heaters may comprise one or more infra-red heaters or one or more combustion heaters. The ion source may further comprise one or more heating devices arranged and adapted to directly and/or indirectly heat the one or more targets or electrodes. The one or more heating devices may comprise one or more lasers arranged and adapted to emit one or more laser beams which impinge upon the one or more targets or electrodes in order to heat the one or more targets or electrodes.

The one or more targets or electrodes may be maintained, in use, at a potential: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV. The one or more targets or electrodes may be maintained, in use, at the above potentials relative to the potential of an enclosure surrounding the ion source and/or an ion inlet device which leads to a first vacuum stage of a mass spectrometer and/or the one or more nebulisers.

The one or more targets or electrodes may be maintained at a positive potential and the droplets impacting upon the one or more targets or electrodes may form a plurality of positively charged ions. Alternatively, according to another mode of operation the one or more targets or electrodes may be maintained at a negative potential and the droplets impacting upon the one or more targets or electrodes form a plurality of negatively charged ions. The ion source may further comprise a device arranged and adapted to apply a sinusoidal or non-sinusoidal AC or RF voltage to the one or more targets or electrodes.

The one or more targets or electrodes may be arranged or otherwise positioned so as to deflect the stream of droplets and/or the plurality of ions towards an ion inlet device of a mass spectrometer. The one or more targets or electrodes may be positioned upstream of an ion inlet device of a mass spectrometer so that ions are deflected towards the direction of the ion inlet device. The one or more targets or electrodes may comprise a stainless steel target, a metal, gold, a non-metallic substance, a semiconductor, a metal or other substance with a carbide coating, an insulator or a ceramic. The one or more targets or electrodes may comprise a plurality of target elements or electrodes so that droplets from the one or more nebulisers cascade upon a plurality of target elements or electrodes and/or wherein the target or electrodes is arranged to have multiple impact points so that droplets are ionised by multiple glancing deflections.

The one or more targets or electrodes may be shaped or have an aerodynamic profile so that gas flowing past the one or more targets or electrodes is directed or deflected towards, parallel to, orthogonal to or away from an ion inlet device of a mass spectrometer. At least some or a majority of the plurality of ions may be arranged so as to become entrained, in use, in the gas flowing past the one or more targets or electrodes. According to an embodiment in a mode of operation droplets from one or more reference or calibrant nebulisers may be directed onto the one or more targets or electrodes. In a mode of operation droplets from one or more analyte nebulisers may be directed onto the one or more targets or electrodes.

A mass spectrometer may be arranged downstream of the impact ionisation source, Electrospray impact ionisation ion source or Gap Electrospray ionisation ion source. The mass spectrometer may comprise an ion inlet device which leads to a first vacuum stage of the mass spectrometer. The ion inlet device may comprises an ion orifice, an ion inlet cone, an ion inlet capillary, an ion inlet heated capillary, an ion tunnel, an ion mobility spectrometer or separator, a differential ion mobility spectrometer, a Field Asymmetric Ion Mobility Spectrometer ("FAIMS") device or other ion inlet.

The one or more targets or electrodes may be located at a first distance $X_1$ in a first direction from the ion inlet device and at a second distance $Z_1$ in a second direction from the ion inlet device, wherein the second direction is orthogonal to the first direction and wherein: (i) $X_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm; and/or (ii) $Z_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm.

The one or more targets or electrodes may be positioned so as to deflect the stream of droplets and/or the plurality of ions towards the ion inlet device. The one or more targets or electrodes may be positioned upstream of the ion inlet device. The one or more targets or electrodes may comprise either: (i) one or more rods; or (ii) one or more pins having a taper cone. The stream of droplets may arranged to impact the one or more rods or the taper cone of the one or more pins either: (i) directly on the centreline of the one or more rods or pins; or (ii) on the side of the one or more rods or the taper cone of the one or more pins which faces towards or away from the ion inlet orifice.

The mass spectrometer may further comprise an enclosure enclosing the one or more nebulisers, the one or more targets or electrodes and the ion inlet device. The mass spectrometer may further comprise one or more deflection or pusher electrodes, wherein in use one or more DC voltages or DC voltage pulses are applied to the one or more deflection or pusher electrodes in order to deflect or urge ions towards an ion inlet device of the mass spectrometer.

It is also contemplated that the above ion sources may be used to at least partially desolvate or further desolvate a stream of droplets. The resulting gas phase molecules and/or secondary droplets may be subsequently ionised by a separate ion source.

For completeness, it will be understood by those skilled in the art that a conventional ion source known as a SACI ion source emits a vapour stream and that the impact velocity of the vapour emitted from a SACI ion source upon a target is relatively low and is approximately 4 m/s. By way of contrast, an impact ionisation ion source according to various embodiments does not emit a vapour stream but instead emits a high density droplet stream. Furthermore, the impact velocity of the droplet stream upon a target or electrode is relatively high and may be approximately 100 m/s. It will be apparent, therefore, that an impact ionisation source according to various embodiments is quite distinct from other types of known ion sources such as SACI ion sources.

According to various embodiments an impact ionisation ion source may be used which converts a liquid stream into a nebulised spray via a concentric flow of high velocity gas without the aid of a high potential difference at the sprayer or nebuliser tip. A micro target or electrode with comparable dimensions or impact zone to the droplet stream may positioned in close proximity (e.g. <5 mm) to the sprayer tip to define an impact zone and to partially deflect the spray towards the ion inlet orifice of a mass spectrometer. The resulting ions and charged droplets may be sampled by the first vacuum stage of the mass spectrometer.

The target or electrode may comprise a stainless steel target or electrode. However, other embodiments are contemplated wherein the target or electrode may comprise other metallic substances (e.g. gold) and non-metallic substances. Embodiments are contemplated, for example, wherein the target or electrode comprises a semiconductor, a metal or other substance with a carbide coating, an insulator or a ceramic.

According to another embodiment the target or electrode may comprise a plurality of plates, target elements or electrodes so that droplets from the nebuliser cascade upon a plurality of target plate, target elements or electrodes. According to this embodiment there may be multiple impact points and droplets may be ionised by multiple glancing deflections.

From an API source perspective, the combination of a close-coupled impact ionisation ion source which also serves as a charged ionization surface provides the basis of a sensitive multimode ionization source. The spray tip and micro target or electrode may be configured in close proximity with a glancing impact geometry which results in increased spray flux at the target or electrode and significantly less beam divergence or reflected dispersion.

The ion sources which may be used according to various embodiments may comprise a multimode ion source which advantageously can ionise high and low polarity analytes at high efficiency without the need to switch hardware or tuning parameters. The droplets which impact the one or more targets or electrodes may be uncharged.

Sequencing Information

Having cleaved intact bovine insulin analyte it was then desired to determine whether enhanced sequencing information could be obtained using a conventional CID gas cell.

The B chain ions produced using an Electrospray impact ionisation described above were analysed by ion mobility MS and MS/MS. According to various embodiments, the product ions produced by Electrospray impact ionisation were analysed using MS.

A mass spectrometer was configured with a quadrupole mass filter for the selection of precursor ions and a following or downstream travelling-wave ion mobility cell (using mbar nitrogen gas) was provided. A CID cell (using argon gas) for fragmentation was arranged downstream of the ion mobility cell and an orthogonal Time of Flight ("TOF") mass spectrometer was arranged downstream of the CID cell for mass analysis.

Figure 15:
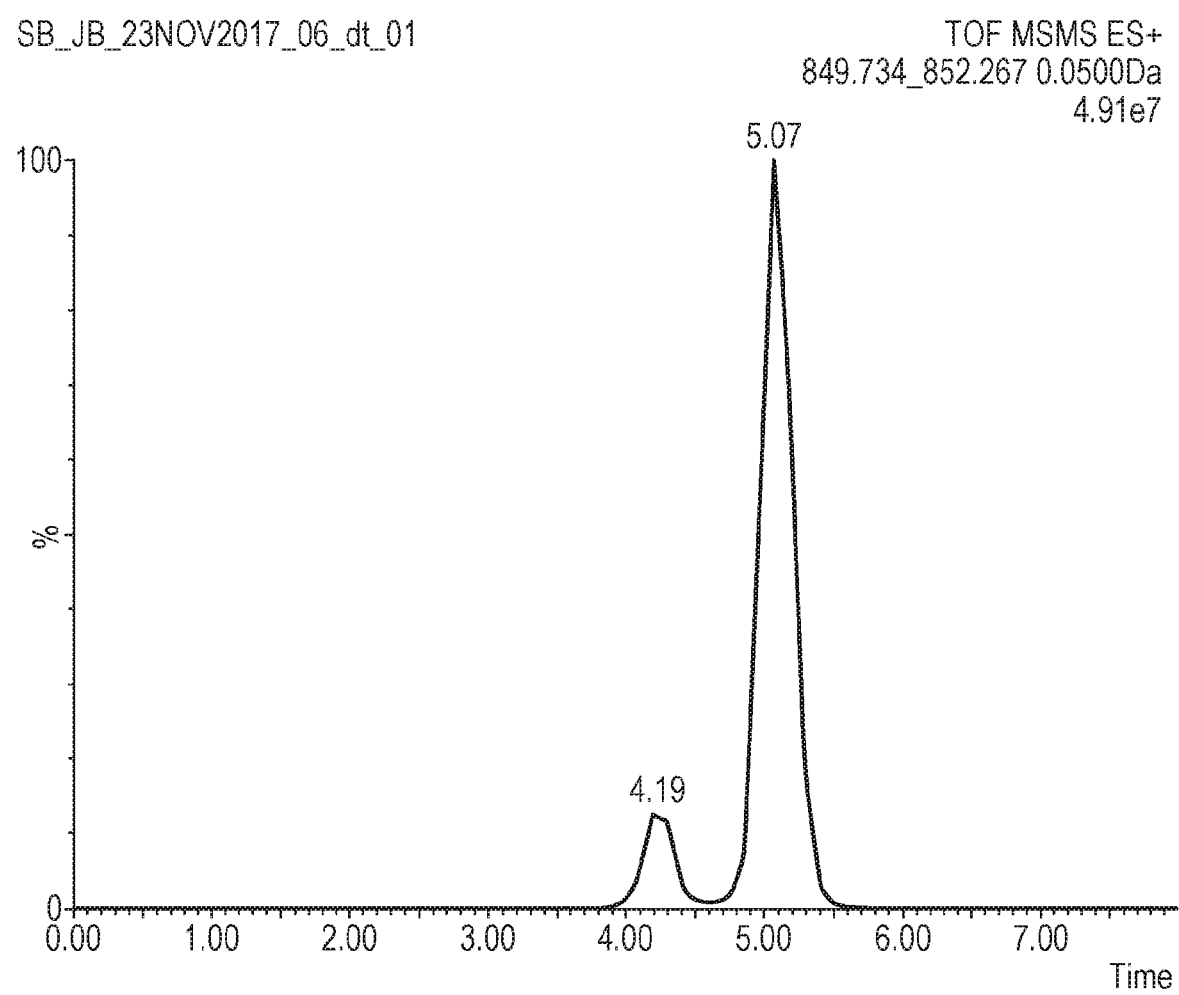
FIG. 15 shows an ion mobility spectrum obtained according to various embodiments from the analysis by ion mobility MS of un-fragmented B chain precursor ions as produced by an Electrospray impact ionisation source used to ionise a bovine insulin sample.

The $[M+4H]^{4+}$ B chain ion envelope was selected with a mass window of 5Th by the mass filter and was analysed by ion mobility MS and MS/MS. As is apparent from the ion mobility spectrum of this envelope, as shown in FIG. 15, the B chain exists in at least two ion conformations as displayed in the two distinct ion mobility peaks.

Figure 16A:
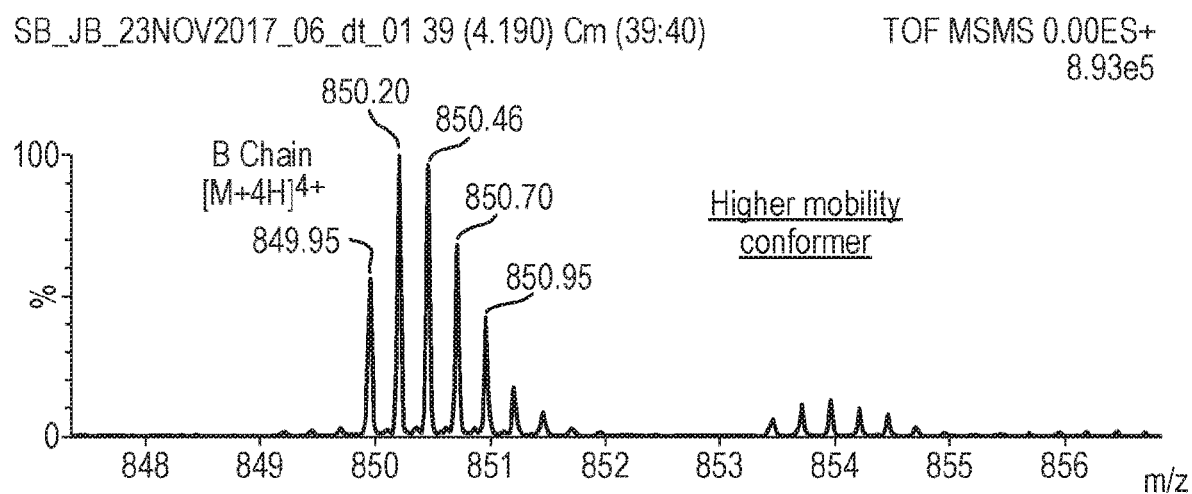
FIG. 16A shows a mass spectrum obtained according to various embodiments from the analysis by an ion mobility MS/MS experiment of the un-fragmented B chain precursor ions in the higher mobility conformation shown in FIG. 15 as produced by an Electrospray impact ionisation source used to ionise a bovine insulin sample and FIG. 16B shows a corresponding mass spectrum obtained according to various embodiments from the lower mobility conformation shown in FIG. 15, wherein the mass spectra reveal a presence of a higher mobility "folded" conformation and a lower mobility "open" conformation.
Figure 16B:
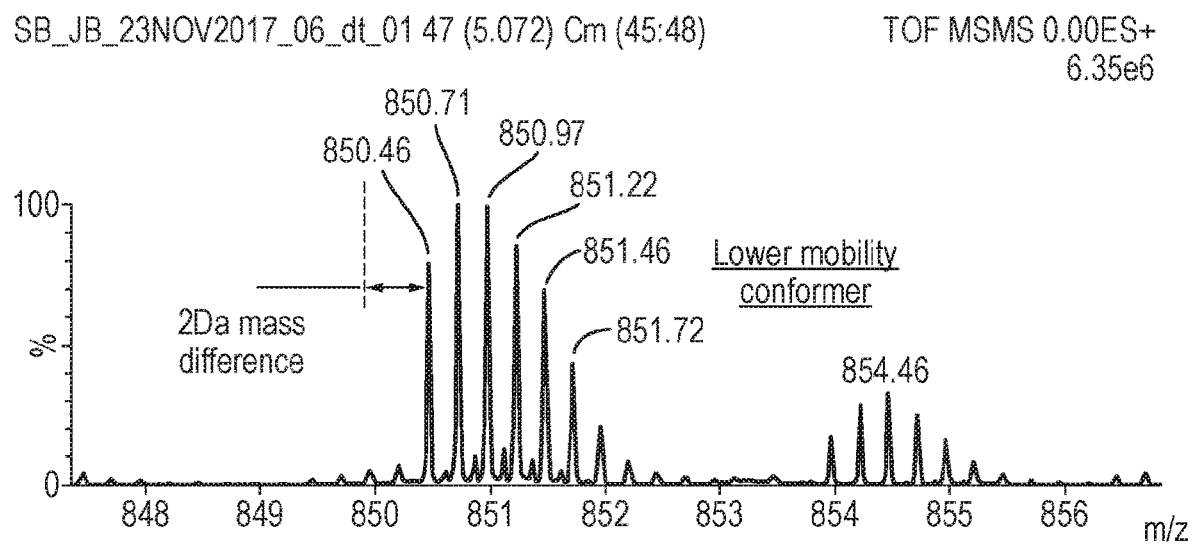

FIGS. 16A and 16B show the resulting mass spectra of the un-fragmented precursor ions for the two conformations from an ion mobility MS/MS experiment. The mass spectrum obtained from the higher mobility peak is shown in FIG. 16A and the mass spectrum obtained from the lower mobility peak is shown in FIG. 16B. As is apparent from comparison of the two mass spectra, there is a mass shift of 2 Da between the higher and lower mobility conformations. Mobility and mass differences between the conformations may be expected to result from the proposed structural schematics for the B chain shown in FIG. 17A and FIG. 17B. Here, the letters correspond to the standard notation for amino acid residues.

The "open" conformation shown in FIG. 17A may exhibit lower ion mobility whilst the "folded" conformation shown in FIG. 17B may exhibit higher ion mobility. The folded conformation may result due to the formation or reformation of an S—S bond between two cysteines of the B chain which would also result in the loss of two hydrogen atoms and hence the 2 Da mass difference between the conformations.

Figure 18A:
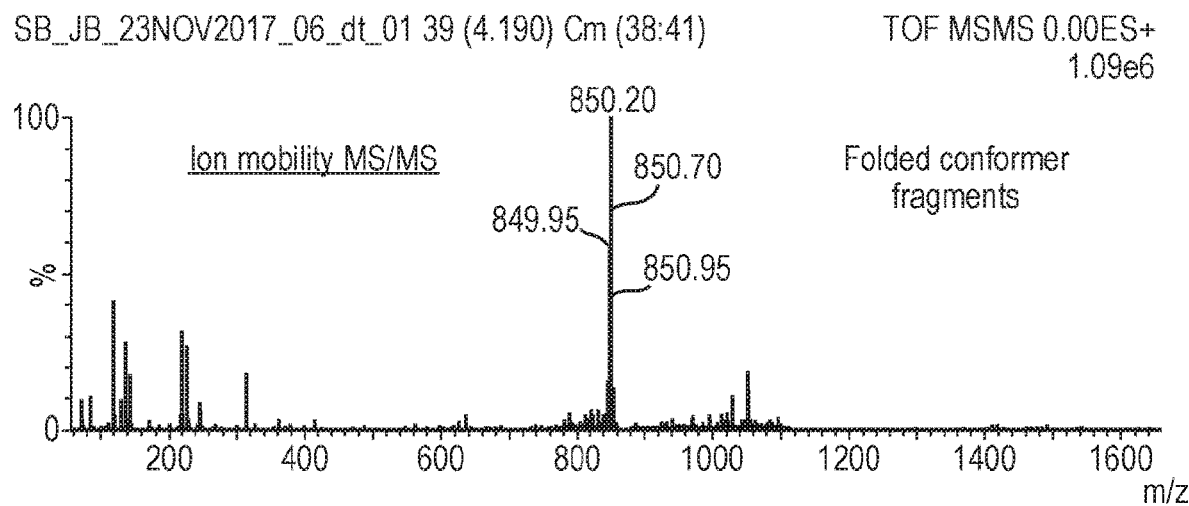
FIG. 18A shows a mass spectrum which was obtained according to various embodiments from ion mobility MS/MS of the folded ion conformation of the bovine insulin B chain produced by an Electrospray impact ionisation source used to ionise a bovine insulin sample and FIG. 18B shows a corresponding mass spectrum obtained according to various embodiments from the open ion conformation of the bovine insulin B chain produced by an Electrospray impact ionisation source used to ionise a bovine insulin sample.
Figure 18B:
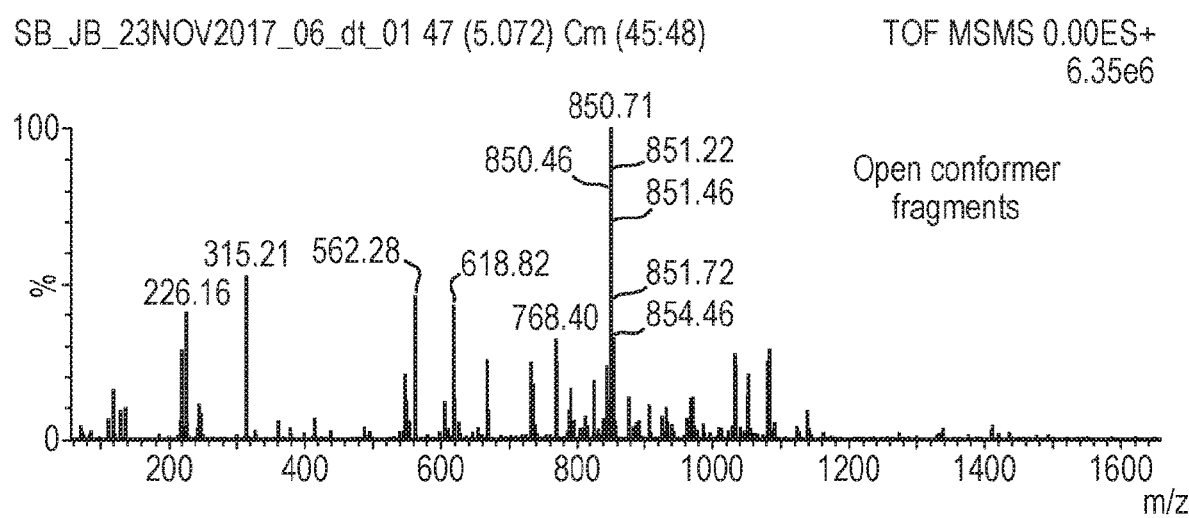

FIGS. 18A and 18B show the full mass spectra obtained for the two conformers in an ion mobility MS/MS experiment. FIG. 18A shows the mass spectrum obtained from the folded conformation and FIG. 18B shows the mass spectrum from the open conformation. It is apparent from the mass spectrum shown in FIG. 18A that the presence of S—S bonds and folded ion conformations may suppress ion fragmentation, while it is apparent from FIG. 18B that the open conformation promotes enhanced fragmentation.

Since the spectra shown in FIGS. 18A and 18B contain ions of a number of different charge states, it is conventional to de-convolute the spectra to a single charge state which greatly simplifies spectral interpretation and fragment assignment.

Figure 19A:
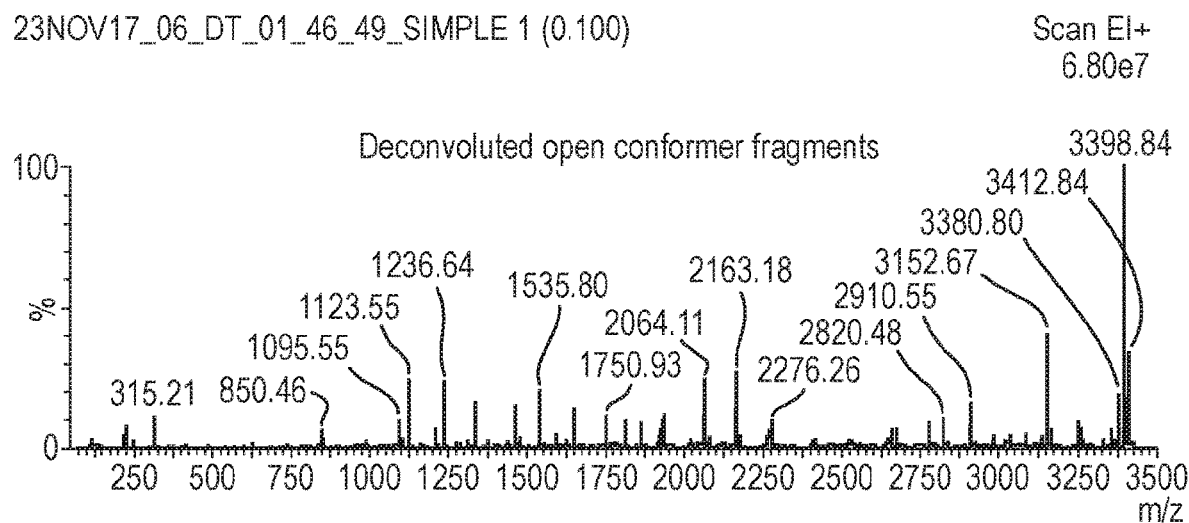
FIG. 19A shows de-convoluted mass spectra obtained from the data shown in FIG. 18B
Figure 19B:
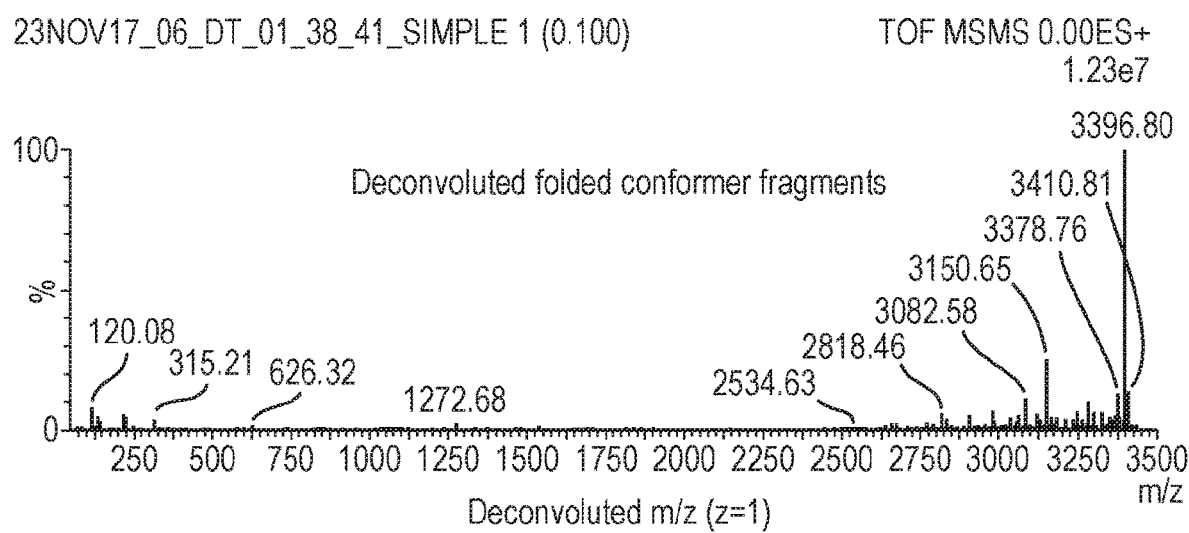
FIG. 19B shows de-convoluted mass spectra obtained from the data shown in FIG. 18A.

FIG. 19A show a de-convoluted mass spectrum obtained from the data shown in FIG. 18B, and FIG. 19B shows a de-convoluted mass spectrum obtained from the data shown in FIG. 18A, both obtained by inputting the data from FIGS. 18A-B into a mass spectral de-convolution algorithm known as "BayeSpray". These spectra clearly indicate that the open conformer fragments across the entire polypeptide chain whilst the folded conformer is limited to only large or small fragments.

The de-convoluted mass spectral data of FIGS. 19A-B can be outputted in a mass/intensity pair format and submitted to a number of commercially available or online protein/peptide sequencing programs that match fragments to a protein candidate sequence. The mass/intensity pair data from FIGS. 19A-B were submitted to the online ProSight Lite program and the resulting sequence information is shown in FIGS. 20A-B. In the notation of FIGS. 20A-B, a solid vertical line between amino acid residues indicates a confirmed backbone cleavage where an upper left hand tick corresponds to a confirmed B ion fragment whilst a lower right hand tick indicates a confirmed Y ion fragment.

As shown by FIG. 20A, the current method gives rise to a complete sequence coverage (100% residue cleavage) for the open conformer of the bovine insulin B chain. This valuable structural information would not be available from conventional CID/MS/MS experiment on the intact bovine insulin precursor ion. In contrast, FIG. 20B shows fragments are only obtained from the "tails" of the folded conformer (59% residue cleavage), i.e. from beyond the loop formed by the S—S bond.

A closer inspection of the deconvoluted mass/intensity pair data reveals that the two confirmed cleavages from within the loop are most probably erroneous since their intensities are low and are comparable to the neighbouring background ions.

In addition to the ion mobility data and the observed mass shift in the MS data, the sequence data of FIG. 20B lends further support to a folded B chain ion conformation as proposed with regard to FIG. 17B.

The observation of a mass shift in the MS/MS spectra can be used to determine the presence of S—S bonds in fragment ions.

Figure 21A:
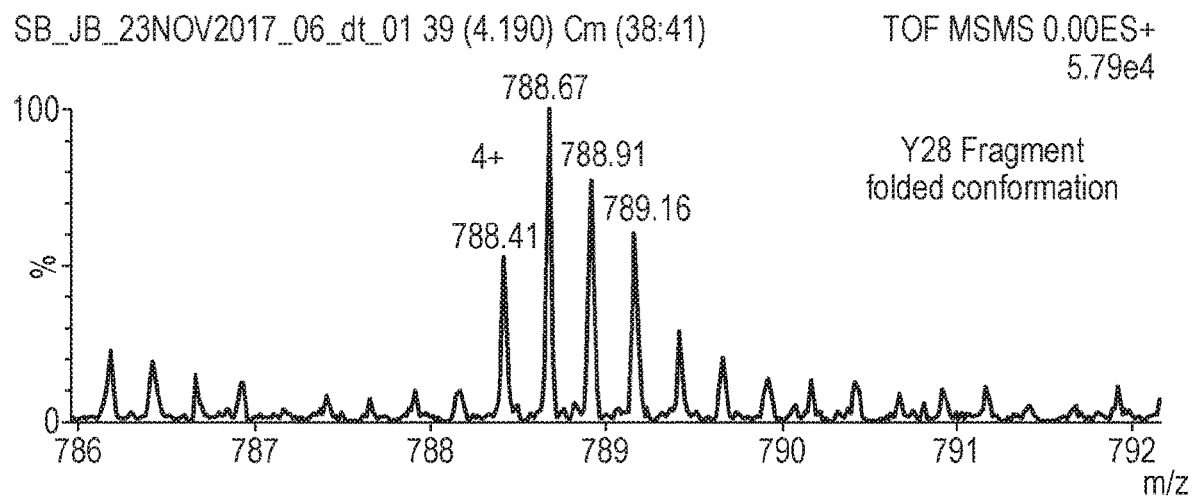
FIG. 21A shows a mass spectrum obtained according to various embodiments from the analysis by MS of Y28 fragments that are derived from the folded conformation of the bovine insulin B chain and FIG. 21B shows a mass spectrum obtained according to various embodiments from the analysis by MS of Y28 fragments that are derived from the open conformation of the bovine insulin B chain.
Figure 21B:
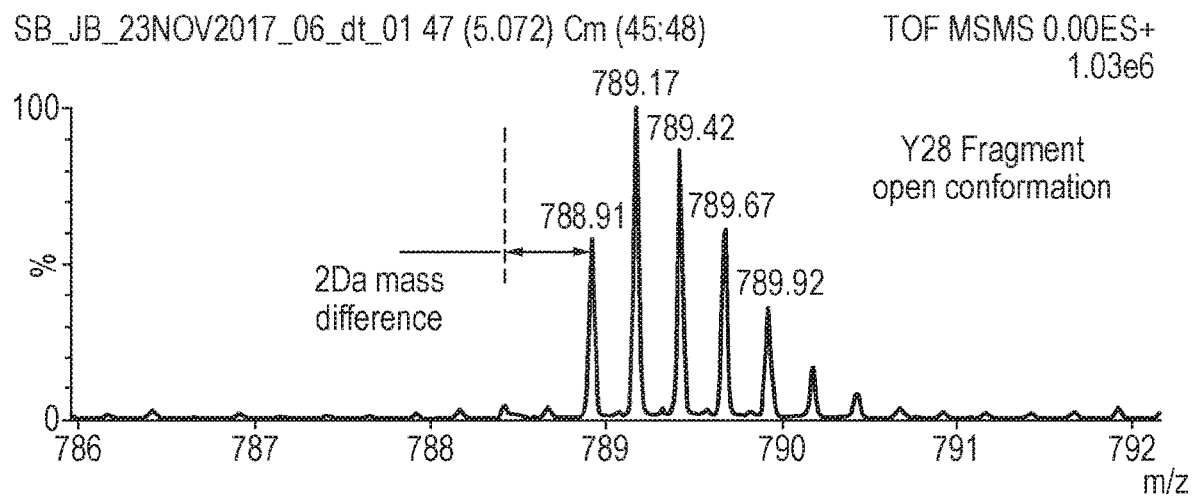

FIG. 21A shows a mass spectrum obtained according to various embodiments from the analysis by MS of Y28 fragments that are derived from the folded conformation of the bovine insulin B chain that exist in a folded conformation and FIG. 21B shows a mass spectra obtained according to various embodiments from the analysis by MS of Y28 fragments that are derived from the open conformation of the bovine insulin B chain that exist in an open conformation.

A comparison of FIG. 21A and FIG. 21B shows a 2 Da mass shift between the Y28 fragments that exist in an open or folded conformation. The mass deficiency in the spectrum of FIG. 21A is indicative of an intact S—S bond in the fragment ion structure.

Figure 22A:
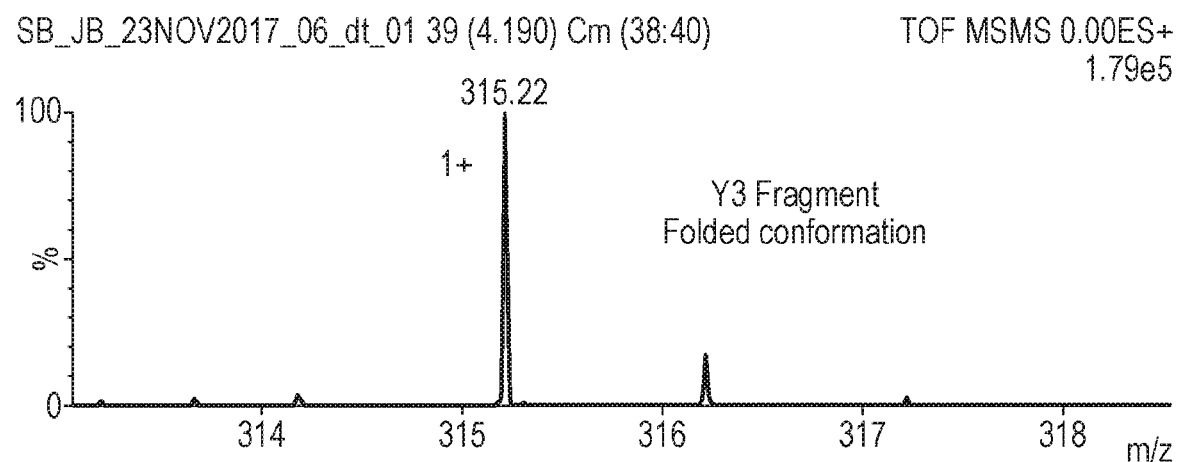
FIG. 22A shows a mass spectrum obtained according to various embodiments from the analysis by MS of Y3 fragments that are derived from beyond the bonded loop of the folded conformation of the bovine insulin B chain and FIG. 22B shows a mass spectrum obtained from according to various embodiments from the analysis by MS of Y3 fragments that are derived from the ends of the open conformation of the bovine insulin B chain.
Figure 22B:
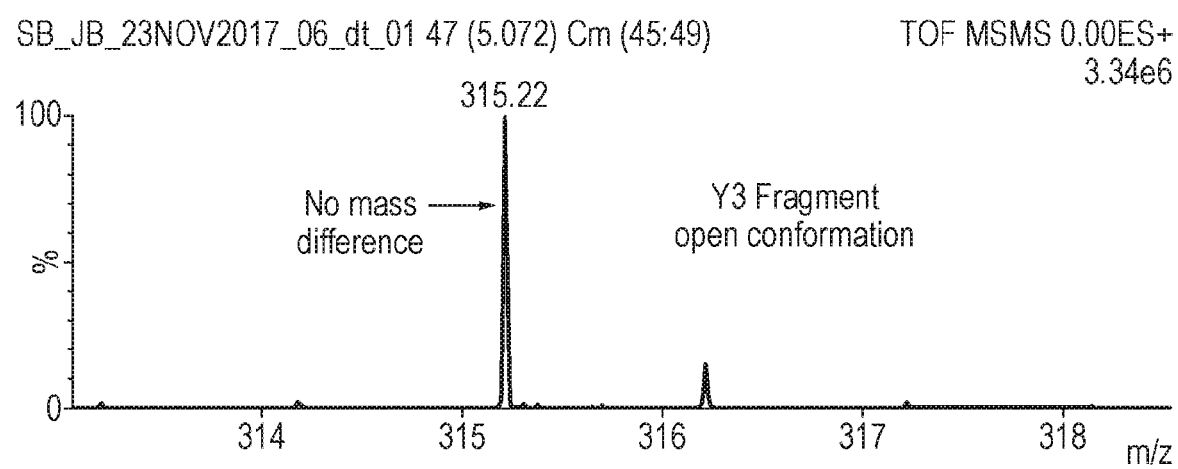

FIG. 22A shows a mass spectrum obtained according to various embodiments from the analysis by MS of Y3 fragments that are derived from beyond the bonded loop of the folded conformation of the bovine insulin B chain and FIG. 22B shows a mass spectrum obtained according to various embodiments from the analysis by MS of Y3 fragments that are derived from the ends of the open conformation of the bovine insulin B chain. As expected, no mass shift is observed by comparison of FIG. 22A and FIG. 22B for the smaller fragments that are derived from the ends of the open conformers, or from beyond the S—S bonded loop in the folded conformers.

It follows that higher mass shifts may be indicative of more than one fold when comparing mass spectra from open versus folded ion conformations. It should also be noted that the same observation of both open and folded ion conformations could be inferred from MS and MS/MS data in the absence of an ion mobility separation. Here, the resulting mass spectrum would exhibit an elongated isotope distribution that deviates from the theoretical distribution expected for either the open or folded conformer.

The various embodiments therefore are particularly advantageous in that the approach according to various embodiments enables the B chain component of bovine insulin molecules to be readily observed and analysed, so as to determine the presence of S—S bonds and evaluate corresponding conformal structure. Accordingly, valuable structural information which would not be available from a conventional CID/MS/MS experiment on the intact bovine insulin precursor ion can be obtained.

A particularly advantageous aspect of the various disclosed embodiments is, therefore, that by using an impact ionisation ion source followed by ion mobility MS and/or MS/MS, it is possible to reveal additional structural information (e.g. detect different conformations of bovine insulin B chain ions or analyse other biomolecules having disulphide bonds) that are not observed using conventional Electrospray ionisation (unless bovine insulin molecules are subjected to a prior cleaving step by chemical reduction).

Electron Bombardment-Initiated Reduction

As discussed above, it is believed that the in-source reduction process is related to discharge currents at the ESI probe tip that result in electron bombardment of the positively charged capillary tip. This process has previously been described by Lloyd and Hess (JASMS (2009), 20, 1988-1996) where the electron bombardment leads to direct ionization of iron (Fe+.) at the capillary tip which then leads to either direct ionization of the analyte or to a series of electrochemical reactions with the solution components.

The small diameter of an electrospray capillary leads to significant electric field enhancement at the tip which, in turn, leads to higher electron bombardment energy. If a window is opened in the front of the source enclosure such that the source environment is no longer sealed, an immediate drop in B chain ion intensity is observed where the signal can drop to less than 20% of its initial intensity.

It is assumed that oxygen from the laboratory environment becomes entrained in the electrospray plume and depletes the free electron population by the formation of negative oxygen ions. Since the oxygen impurity level of nitrogen generating systems may fluctuate depending on overall demand (output), a preferred method for the in-source reduction of biomolecular ions is to utilise a high-purity nitrogen source for the nebulizer and desolvation heater gases.

Further evidence in support of an electron bombardment-initiated reduction mechanism may be obtained by comparing B chain ion intensities between an Electrospray impactor ion source and a conventional Impactor ionization source. In a conventional impactor ion source (see e.g. FIG. 1), the liquid capillary may be grounded and the high voltage is applied to the target i.e. a reverse of the arrangement shown in FIG. 12B.

In this case, electrons in the discharge will bombard the relatively "flat" surface of the impactor, which may have Ø1.6 mm, where the electric field and hence electron energy is significantly lower than at the tip. Additionally, the electron bombardment may occur over a wider area (reduced flux) due to the diverging nature of the field in the electrode gap.

As a result, a conventional Impactor spray source does not produce significant B chain ion intensities using the method described above. However, it can be shown that by introducing a flow of helium gas into the electrode gap via a nylon tube in an open source enclosure arrangement, the conventional Impactor source can produce comparable B chain ion intensities to a nitrogen-fed Electrospray impactor ion source.

Under these conditions, He produces an enhanced discharge that can be seen at the surface of the Impactor where B chain ions are created as described above. In an embodiment He, or nitrogen with a percentage of He, may be used as the nebuliser gas in a sealed Impactor source.

Furthermore, the use of He or $N_2$/He mixtures as a nebulizing gas may also be beneficial for the Electrospray ionisation source shown in FIG. 12A the Electrospray impact ionisation ion source shown in FIG. 12B and the Gap Electrospray ion source shown in FIG. 12C. Finally, in the case of a conventional Impactor source, the use of a small field enhancing feature (e.g. sharp point) or features on the surface of the impactor may further enhance ion reduction by increasing the localized flux and energy of the electron bombardment.

Alternatives

It is known to operate a conventional Electrospray ionisation ("ESI") ion source at high voltages (5-10 kV) in order to induce breakdown wherein oxygen gas is then added to the source in order to study oxidation of proteins or the binding of protein complexes. For example, reference is made to an Electrospray ionisation ("ESI") ion source for protein analysis as disclosed in Anal. Chem. 2003, 75, 1557-1563. Such an approach may also be adopted with the apparatus and methods according to various embodiments as disclosed in the present application.

With reference to known discharging Electrospray ionisation ("ESI") sources, it will be understood by those skilled in the art that energetic visible discharges are hard to replicate and can vary from one instrument to the other depending on the state of various components and other parameters such as surface cleanliness, etc. In addition, the nature of the discharge may change with time due to degradation of the discharge components. These effects will hamper the reproducibility of analyses conducted on such instrumentation.

Breaking S—S Bonds

Although the various embodiments disclosed above are focused upon the analysis of bovine insulin and monoclonal antibodies, the apparatus and methods disclosed in the present application are also applicable to a wide range of biomolecules (especially biomolecules having one or more disulphide bonds) and not just bovine insulin or monoclonal antibody molecules.

The methods according to the various embodiments disclosed above enable certain ion fragment species or certain ion conformations obtained from precursor biomolecules that may contain S—S bonds to be produced via a simple process without requiring complex and time consuming sample preparation steps to be performed and/or without requiring alternative or complimentary techniques such as chemical reduction, electron capture dissociation ("ECD") or electrochemical cell technology.

The various embodiments therefore are particularly advantageous in that the approach according to various embodiments enables fragment ions of precursor biomolecules obtained by the breaking of S—S bonds to be readily observed by simply ionising a sample of the biomolecule without requiring complex and time consuming sample preparation steps to be performed and/or without needing to subject the sample to alternative or complimentary techniques such as chemical reduction, electron capture dissociation ("ECD") or electrochemical cell technology.

It will be understood, therefore, by those skilled in the art that the ability to straightforwardly and simply produce, recognise and analyse both parent intact biomolecule ions and associated fragment ions obtained by the breaking of S—S bonds represents a significant advance in the art.

Although the present invention has been described with reference to preferred embodiments, it will be understood by those skilled in the art that various changes in form and detail may be made without departing from the scope of the invention as set forth in the accompanying claims.

The invention claimed is:

1. A method of ionising a sample comprising:
   nebulising a sample which includes first biomolecules comprising one or more disulphide (S—S) bonds; and
   directing a stream of droplets or charged droplets having one or more disulphide (S—S) bonds so as to pass through an electric field region so as to cause the breaking of a portion of the disulphide bonds, wherein the electric field region is determined by an electrode and an ion inlet of a mass spectrometer, and wherein the electrode is arranged downstream of a nebuliser or electrospray probe.

2. A method as claimed in claim 1, wherein the electrode comprises aluminium.

3. A method as claimed in claim 1, further comprising introducing helium gas or a mixture including helium gas either: (i) into a nebuliser which is arranged to nebulise the sample; (ii) into the vicinity of the electrode; or (iii) into the electric field region.

4. A method as claimed in claim 1, wherein the electrode comprises one or more field enhancing features.

5. A method as claimed in claim 4, wherein the one or more field enhancing features comprise one or more spikes, projections or sharp points.

6. A method as claimed in claim 1, wherein the breaking of a portion of the disulphide bonds results in the fragmentation of a portion of the first biomolecules and/or conformational changes so as to form product or analyte ions.

7. A method as claimed in claim 6, wherein the product or analyte ions comprise one or more of the following: (i) intact parent ions; (ii) A chain fragment ions; (iii) B chain fragment ions; (iv) modified parent ions; and (v) conformationally modified parent ions.

8. A method as claimed in claim 1, wherein the first biomolecules comprise insulin molecules, bovine insulin molecules, human insulin molecules, equine insulin molecules, porcine insulin molecules, synthetic insulin molecules, monoclonal antibody molecules or Lysozyme.

9. A method as claimed in claim 1, wherein the step of nebulising the sample comprises using a Gap Electrospray ionisation ion source having a nebuliser or electrospray probe, wherein a first voltage is applied to the nebuliser or electrospray probe and a second lower, different or zero voltage is applied to the electrode.

10. A method as claimed in claim 1, further comprising mass or mass to charge ratio selecting, filtering or otherwise preferentially selecting one or more species of product or analyte ions and optionally attenuating one or more other species of product or analyte ions.

11. A method as claimed in claim 10, wherein the step of mass or mass to charge ratio selecting, filtering or otherwise preferentially selecting one or more species of product or analyte ions comprises using a quadrupole mass filter to select product or analyte ions having a particular mass to charge ratio or range of mass to charge ratios.

12. A method as claimed in claim 10, wherein the step of mass or mass to charge ratio selecting, filtering or otherwise preferentially selecting one or more species of product or analyte ions comprises selecting, filtering or otherwise preferentially selecting either: (i) intact parent ions; and/or (ii) A chain fragment ions; and/or (iii) B chain fragment ions; and/or (iv) modified parent ions; and/or (v) conformationally modified parent ions.

13. A method as claimed in claim 10, further comprising temporally separating one or more species of product or analyte ions according to their ion mobility, differential ion mobility or collision cross section.

14. The method of claim 1, wherein nebulising the sample comprises using a Gap Electrospray ionisation ion source having a nebuliser or electrospray probe; wherein directing the stream of droplets or charged droplets comprises directing the stream of droplets or charged droplets so as to pass through the electric field region without substantially impacting the electrode; and wherein a first voltage which is in the range of 3.0-6.0 kV is applied to the nebuliser or electrospray probe, and the electrode is grounded.

15. A Gap Electrospray ionisation ion source comprising:
   a nebuliser or electrospray probe configured to nebulise a sample;
   an electrode arranged downstream of the nebuliser or electrospray probe; and
   an electric field region determined by the electrode and an ion inlet of a mass spectrometer;
   wherein the ion source is configured to direct a stream of charged droplets of first biomolecules comprising one or more disulphide (S—S) bonds so as to pass through the electric field region without substantially impacting the electrode so as to form product or analyte ions; and
   wherein a first voltage which is in the range of 3.0-6.0 kV is applied to the nebuliser or electrospray probe, and the electrode is grounded.

16. An ion source as claimed in claim 15, further comprising a device configured to introduce helium gas or a mixture including helium gas either: (i) into the nebuliser or electrospray probe; or (ii) into the electric field region.

17. A mass spectrometer comprising an ion source as claimed in claim 15, and a mass or mass to charge ratio filter configured to select, filter or otherwise preferentially select one or more species of product or analyte ions and optionally attenuate one or more other species of product or analyte ions.

18. A mass spectrometer as claimed in claim 17, further comprising a device configured to temporally separate one or more species of product or analyte ions according to their ion mobility, differential ion mobility or collision cross section.

19. An ion source comprising:
- a nebuliser or electrospray probe configured to nebulise a sample;
- an electrode arranged downstream, and off-axis, of the nebuliser or electrospray probe; and
- an electric field region determined by the electrode and an ion inlet of a mass spectrometer;
- wherein the ion source is configured to direct a stream of droplets or charged droplets generated by the nebuliser or electrospray probe between the electrode and the ion inlet of the mass spectrometer so as to pass through the electric field region without substantially impacting the electrode so as to form product or analyte ions; and
- wherein a first voltage which is in the range of 3.0-6.0 kV is applied to the nebuliser or electrospray probe, and the electrode is grounded.

* * * * *